(12) United States Patent
Carvalho et al.

(10) Patent No.: US 8,541,395 B2
(45) Date of Patent: Sep. 24, 2013

(54) USE OF TELOCINOBUFAGIN AS AN ANALGESIC IN THE TREATMENT OF ACUTE AND CHRONIC PAINS

(75) Inventors: Krishnamurti De Morais Carvalho, Fortaleza (BR); Dòris Maria Fernandes Carvalho, Fortaleza (BR); Maria Denise Fernandes Carvalho, Fortaleza (BR); Ogari de Castro Pacheco, Itapira (BR); Roberto Carlos Debom Moreira, Itapira (BR)

(73) Assignees: Cristalia Produtos Quimicos Farmaceuticos Ltda., Itapira (BR); Genpharma Consultoria Farmaceutica E Genetica Ltda., Fortaleza (BR)

( * ) Notice: Subject to any disclaimer, the term of this patent is extended or adjusted under 35 U.S.C. 154(b) by 93 days.

(21) Appl. No.: 13/322,917

(22) PCT Filed: May 26, 2010

(86) PCT No.: PCT/BR2010/000169
§ 371 (c)(1),
(2), (4) Date: Nov. 28, 2011

(87) PCT Pub. No.: WO2010/135798
PCT Pub. Date: Dec. 2, 2010

(65) Prior Publication Data
US 2012/0077788 A1    Mar. 29, 2012

(30) Foreign Application Priority Data

May 28, 2009 (BR) ..................................... 0901758

(51) Int. Cl.
*A61K 31/585* (2006.01)

(52) U.S. Cl.
USPC ............................................................ 514/75

(58) Field of Classification Search
USPC ............................................................. 514/75
See application file for complete search history.

(56) References Cited

PUBLICATIONS

Filho et al. Antimicrobial activity of the bufadienolides marinobufain and telocinobufagin isolated as major components from skin secretion of the toad Bufo rebescens Toxicon 45(2005) 777-782.*

* cited by examiner

*Primary Examiner* — Jennifer M Kim
(74) *Attorney, Agent, or Firm* — Birch, Stewart, Kolasch & Birch, LLP.

(57) ABSTRACT

The present invention is directed to the use of telocinobufagin, or its pharmaceutically acceptable derivatives, in the manufacture of a medicament for the treatment or prevention of acute and chronic pains. The present invention also refers to a pharmaceutical composition comprising an effective amount of telocinobufagin; also provides a method to induce analgesia in response to acute and chronic pains that comprehends administering an effective amount of telocinobufagin to human beings or animals. According to the outcomes of in vivo assays, telocinobufagin is more potent than morphine, though without presenting the known side effects of opioids. In addition, in vivo and in vitro essays showed that TBC does not present cardiotoxicity.

4 Claims, 16 Drawing Sheets

USE OF TELOCINOBUFAGIN AS AN ANALGESIC IN THE TREATMENT OF ACUTE AND CHRONIC PAINS

This application is the National Stage under 35 U.S.C. §371 of International Application Number PCT/BR2010/000169 filed on May 26, 2010, which claims priority under 35 U.S.C. §119(a)-(d) of application number PI0901758-5 filed on May 28, 2009 in Brazil.

The present invention refers to the field of analgesia and treatment or prevention of pain.

The present invention is directed to the use of telocinobufagin (TCB), or its pharmaceutically acceptable derivatives, in the manufacture of a medicament for the treatment or prevention of pain in human beings and animals. Additionally, the present invention is directed to the use of telocinobufagin, or its pharmaceutically acceptable derivatives, as an analgesic for acute and chronic pains. The present invention also refers to a pharmaceutical composition containing an effective amount of telocinobufagin, or its pharmaceutically acceptable derivatives, and pharmaceutically acceptable excipients.

According to another incorporation of the present invention, a method for the treatment or prevention of acute and chronic pains is provided, which comprises the administration of an effective amount of telocinobufagin, or its pharmaceutically acceptable derivatives, to human beings or animals in need of the referred treatment.

According to the International Association for the Study of Pain (IASP), pain is characterized as "an unpleasant sensory and emotional experience associated with actual or potential tissue damage or described in terms of such damage." [Loeser, J. D., Melzack, R. 1979. *Pain: an overview. Lancet* 353: 1607-1609]. Physiologically, it acts as an important warning, leading to defense and preservation reactions.

Pain is a symptom of several clinical disorders and affects great share of the population. It is usually responsible for a significant share of health services demand and constitutes a multifactorial phenomenon, involving psychosocial, behavioral and physiopathological processes.

In addition to involving a potentially noxious stimulus, pain has an individual connotation and is represented by a subjective experience, including affective and emotional behaviors, which amplify or reduce the painful sensation [Almeida, R. f. Roizenblatt, S., Tufik, S. 2004. Afferent pain pathways: a neuroanatomical review. Brain Res 1000:40-56].

To facilitate the communication and data interpretation, the IASP has developed a taxonomy that classifies pain in five main axes, according to the affected region, the involved system, its temporal characteristics, its intensity reported by the patient, and the pain etiology.

Regarding the region, pain can affect the head, face, mouth, cervical region, shoulders and upper limbs, thoracic region, abdominal region, lumbosacral spine, coccyx, lower limbs, pelvic region, and perineal, anal and genital region.

Regarding the system, pain can involve the nervous system (central, peripheral and/or neurovegetative), psychological and social factors, respiratory and/or cardiovascular system, musculoskeletal and/or glandular tissue, gastrointestinal system, genitourinary system, and other organs or viscera.

Regarding the temporal characteristics, pain can be continuous or almost continuous without fluctuations, continuous with exacerbations, recurrent with regularity, recurrent without regularity, paroxysmal, and combinations thereof.

Regarding the intensity, the pain reported by the patient can be mild, moderate and intense.

Regarding the etiology, pain may be caused by congenital or genetic disorders; traumas, surgeries or burns; infectious and/or parasitic disease; metabolic disease; inflammation; autoimmune disease; neoplastic disease; intoxications; metabolic alterations and diseases; degenerative conditions; dysfunctional conditions; psychological disturbances, and unknown causes.

In addition to these categories, pain is also classified regarding its duration or evolution, as being acute or chronic. Acute pain has physiological nature, is triggered by tissue injury and has a warning and defense role. It is mediated by thermal, mechanical or chemical stimulation of the nociceptors. It usually has a short duration, and may be of two types: neurogenic, when it is caused by a peripheral nociceptive stimulus, or inflammatory, when it is caused by an inflammatory reaction. Therefore, acute pain has a well determined cause-effect relationship, and is characterized by the fact of being punctual, delimited and by disappearing with the resolution of the pathological process. Chronic pain is gradually incapacitating because it may persist for an extended period of time and, in some cases, it is associated with the alteration of the central mechanisms of nociception. It may exist or persist in the absence of an actual lesion, produces persistent alterations in the psychomotor (emotional) behavior and may lead to permanent physical and mental impairment [Almeida, R. F. Roizenblatt, S., Tufik, S. 2004. Afferent pain pathways: a neuroanatomical review. Brain Res 1000:40-56].

The most common chronic pains include those of oncologic origin, those associated with myofascial pain syndrome, headache, fibromyalgia, pain associated with rheumatoid arthritis, phantom limb pain, central pain syndromes and neuropathic pain [Ashburn, M. A.; Staats, P. S. 1999. *Management of chronic pain. Lancet*, v. 353, p. 1865-1869,].

Neuropathic pains are always chronic and result from neural lesion or dysfunction of neural circuits of pain. In these cases, there is no tissue damage, but anomalous activation of the neural pathways that transmit pain information. The patients describe such pains as a burning sensation, pin or needle perforation, electric shocks or numbness. They tend to occur in cutaneous regions corresponding to the dermatomes and may not respond well to opioids. Psychogenic pains, on the other hand, are usually chronic, associated with depressive and/or conversive conditions, and do not fit into the mechanisms described above.

In 1994, the IASP proposed a definition of neuropathic pain, as being a pain of neural origin due to a primary lesion or dysfunction in the nervous system [Merskey H, Bogduk N. 1994. *Classification of Chronic Pain,* 2nd ed. Seattle: IASP Press, 394]. Neuropathic pain may be caused by damage to the peripheral nerves and nerve roots, spinal cord, encephalic trunk and brain. It is a complex and heterogeneous entity, with signs and symptoms that may range in intensity over time. Neuropathic pain is associated with several pathological states (Table 1) and its clinical presentation is associated with several other symptoms.

TABLE 1

Traditional etiological classification of neuropathic pain.

| Classification | Characteristic/Prevalence |
| --- | --- |
| Trauma | Phantom limb, spinal cord damage. |
| Ischemic injury | Central pain, painful diabetic neuropathy. |
| Infection/inflammation | Post-herpetic neuralgia, HIV. |
| Cancer | Invasion/compression of neural |

TABLE 1-continued

Traditional etiological classification of neuropathic pain.

| Classification | Characteristic/Prevalence |
| --- | --- |
| Medications | structures<br>Vinca alkaloids. |
| Compression | Sciatic, trigeminal neuralgia. |
| Unknown | Trigeminal neuralgia. |

Neuropathic pain is frequently described as having a continuous or pungent burning nature, and it is commonly associated with allodynia and/or hyperalgesia. Allodynia is defined as pain in response to a stimulus that usually does not cause pain (non-injurious), and hyperalgesia is defined as an exacerbated sensitivity to a painful (injurious) stimulus.

Pain is a very prevalent symptom in patients with neoplasias. It is present in 50% to 70% of individuals with neoplasias in general, and up to 90% of individuals with more advanced stages of the disease. Pains associated with neoplasias are usually intense and result from mechanisms such as: invasion and/or compression of nerves, bones and soft tissues; obstruction and/or distension of hollow viscera; paraneoplastic neuropathies; and toxic or inflammatory neuropathies resulting from surgeries, chemotherapy or radiotherapy. More than two thirds of the cases of pain associated with cancer result from a direct tumor aggression, and a quarter of the cases result from antineoplastic treatments. Such pains are multifaceted, and may be classified as acute, chronic, nociceptive, neuropathic or psychogenic.

Nociceptive pains (the term nociceptive is derived from the Latin word nocere, which means "to damage") are acute or chronic, and result from tissue damage due to trauma, inflammation or compression (herniations and tumors). Such processes promote a physiological stimulation of free nerve endings in any body region innervated by them. Its intensity is proportional to the activation degree of the receptor and it is usually well controlled with opioids. [*ESMO. Management of cancer pain: ESMO Clinical Recommendations. Annals of Oncology.* 2007. 18(Suppl 2): ii92-ii94. Polomano, R. C. Farrar, J. T, 2006. Pain and neuropathy in cancer survivors. Am. J. Nurs., 106 (3 Suppl): 39-47].

There are several effective medications for the treatment of acute pain caused by different etiologies, such as opioids and nonsteroidal antiinflammatory drugs (NSAIDs). The therapeutic options for neuropathic pains are less effective or less tolerable. Due to their distinct pathophysiological mechanisms, agents that are useful in the treatment of other types of pains have only limited efficacy in the treatment of neuropathic pain.

Morphine, for example, is widely used for the administration in cases of severe acute pain due to its worldwide availability, extensive clinical experience, significant pharmacokinetic and pharmacodynamic data, low cost and several sustained-release formulations. However, the incidence and severity of the adverse effects, among others, the tolerance phenomenon (need of increasing doses for maintenance of the effect), dependence (physical and emotional need of use), nausea, constipation, itching, somnolence and respiratory depression, may be limiting factors of its therapeutic use.

In particular, opioids have lower efficacy in the treatment of neuropathic pain than in the treatment of inflammatory pain [Bridges, D., Thompson, S. W. N., Rice, A. S. C. 2001. Mechanisms of neuropathic pain. British Journal of Anaesthesia 87 (1): 12-26] [Sindrup S. H., Jensen, T. S. 1999. Efficacy of pharmacological treatments of neuropathic pain: an update effect related to mechanism of drug action. Pain; 83: 389-400].

The class of NSAIDs is highly effective for the treatment of acute pain and mild and moderate chronic pain. The main mechanism by which NSAIDs exert an analgesic effect is the inhibition of the synthesis of certain prostaglandins or prostanoids. The synthesis of prostanoids uses two distinct cyclooxygenase enzymes (COX): COX-1 and COX-2. Traditional NSAIDs inhibit both enzymes. They may also inhibit other lipogenic enzymes, such as 5-lipooxygenase. Although NSAIDs do not cause dependence, they have significant toxic effects, such as gastrointestinal lesions, nephrotoxicity and platelet aggregation inhibition.

Alternatively, the main classes of adjuvant analgesics that are currently used to aid the treatment of neuropathic pain include antidepressants, anticonvulsants, local anesthetics, muscular relaxants and sympatholytics, among others [Max, M. B. 1994. *In: Progress in Pain Research and Management* (Ed, Fields H. L., Liebskind J. C.) IASP Press, Seattle, 229].

Some anticonvulsants used in the treatment of neuropathic pain are: a) carbamazepine, which has central and peripheral effects, but presents a high incidence of adverse effects associated with the central nervous system (blurred vision, dizziness, headache, mental confusion, nauseas, etc.), and a high interaction potential with other drugs; b) oxcarbazepine, which is safer than the carbamazepine, but may cause serious damages in patients with renal failure, as well as reduction in the plasma sodium levels, leucopenia, thrombocytopenia and cutaneous rash; c) phenyloin, which is more potent than carbamazepine; however, due to the phenomenon known as zero-order kinetics, the enzymatic system responsible by drug metabolism is saturated as the serum concentration increases, making that small dose increments cause great elevations in the drug serum levels, with the respective undesirable collateral effects; d) gabapentin, which is considered one of the safest medications from a pharmacokinetic point of view; however, as high doses are needed for the treatment, the cost is usually impracticable. In addition, it is usually necessary the combination with other drugs.

However, the currently available treatments show limited efficacy (complete relief of pain is rarely achieved) and there is high incidence of debilitating adverse effects, such as those mentioned before.

Due to the complexity of the physiopathology of pain, intense acute and chronic pains are hardly ever treated efficaciously using a single agent. The association of different pharmacological agents with different mechanisms of action is common in the clinical practice. One strategy, for example, involves the use of low doses of opioid analgesics in combination with analgesic doses of one or more non-opioid drugs. This approach provides a better analgesic profile with lower incidence of adverse effects and intolerance, but involves the risks associated with multi-therapy.

Additionally, several other drugs have been used in the treatment of pain, including neuroactive steroids, beta-adrenergic agonists, selective prostanoid receptor antagonists; NMDA antagonists; neuronal nicotinic receptor agonists; calcium channel antagonists; serotonin 5-HT receptor agonist (1B/1D); cannabinoid agonists; superoxide dismutase mimetics; P38 MAP kinase inhibitors; triptans, TRPV1 agonists, ketamine, NK1 receptor antagonists; gabapentinoids, and glycine receptor antagonists.

In this way, it is possible to affirm that the treatment of neuropathic pain is usually difficult and often disappointing. For these reasons, in addition to medications, patients with neuropathic pain frequently need, for example, neurosurgical measures, anesthetic blockages, regional infusion of sympatholytics, infiltrations, neurostimulation with electrodes, acupuncture, intrathecal drug infusions, and physiatric, psychological and occupational therapies, which help them coping with the pain.

Therefore, there still is an actual need for more effective and safer treatments to resolve the problem of pain, especially intense acute and chronic pain. In this context, the present invention describes the use of telocinobufagin as an effective and safe analgesic for use in the treatment or prevention of pain, both acute and chronic.

Telocinobufagin (TBC), whose chemical name is (3β,5β)-3,5,14-trihydroxy-bufa-20,22-dienolide, belongs to the class of bufadienolide steroids and its CAS Registry Number is 472-26-4. The molecular formula of telocinobufagin is $C_{24}H_{34}O_5$, its molecular weight is 402.52, and its structural formula (Formula I) is presented below:

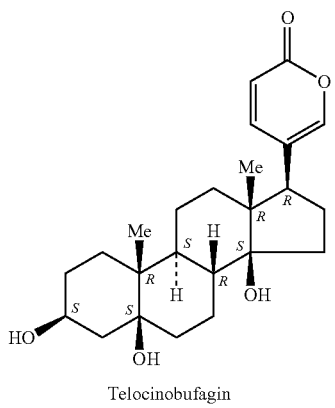

Formula I

Telocinobufagin

Telocinobufagin was first described by Meyer in 1949 together with other bufadienolides (cinobufagin, bufalin, bufotalin and cinobufotalin), all of them isolated from toad venom and presenting digitalis-like properties. The compounds were isolated from the traditional Ch'an Su tea, a preparation that contains toad venom (Ch'an Su in Chinese and Senso in Japanese) [Meyer, K. 1949. *Cardioactive toad poisons (bufogenin). I. Isolation of the cardioactive principles of Ch'an Su (senso). Pharmaceutica Acta Helvetiae*, 24: 222-46 and *Cardiac-active toad poisons (bufogenins). II. Constitution of bufalin*. Meyer, K. 1949. Helvetica Chimica Acta, 32: 1238-45].

Its synthesis was first presented by Pettit, in 1974, who described a synthetic pathway starting from digitoxigenin, passing through bufalin and scillarenin, until reaching to telocinobufagin. As scillarenin is potentially available from the natural glycoside proscillaridin A, the described synthesis permits an easier access to telocinobufagin and related substances [Pettit, G. R., Kamano, Y. Bufadienolides. 27. 1974. *Synthesis of Telocinobufagin. J. Org. Chem.*, 39 (17): 2632-2634].

The term bufadienolide refers to a class of steroids that occur in the venom and skin of amphibians, and in some plant tissue extracts. They have also been isolated from vegetables, fruits and snakes. Bufadienolides consist of a steroid ring bound to a six-member lactone group.

In animals, bufadienolides are widely diffused in the Bufonidae family and several of these compounds have been isolated from the genus *Bufo*, the majority of them being steroid derivatives. For example, Rossi et al. identified the following compounds in the venom of the paratoid glands of *Bufo paracnemis*: sitosterol, argentinogenin, bufalin, bufotalinin, gamabufotalin, hellebrigenin, hellebrigenol, marinobufogenin, resinobufogenin and telocinobufagin. [Rossi. H., Blumenthal, E. E. A., Jared, C. 1997. *Bufodienolides from the venom of Bufo paracnemis* [amphibia, anura, bufonidae]. Anais Assoc. Bras. Quim, 46 (1): 21-26].

The medical-pharmaceutical potential of products derived from the toxic secretions of the genus *Bufo* is well known. Historical reports reveal the therapeutic use of a commercial preparation obtained from dry *Bufo gargarizans* toad venom, the secular Ch'an Su (or Senso). It is probably the first and most ancient therapeutic use of a venom of animal origin. Its applications are much diversified and involve skin wounds healing, the control of mucosal hemorrhages and colds. It has also been used in the treatment of cardiac diseases, but this use was further abolished for presenting no advantages over digitalis compounds [Hong, Z, Chan, K, Yeung, H. W. 1992. Simultaneous determination of Bufadienolides. In: *the traditional Chinese medicine preparation, Liu-Shen-wan, by liquid chromatography. J. Pharm. Pharmacol*, 44: 1023-1026].

Bufogenins and bufotoxins act in a similar manner to digitalis extracts and are cardiotoxic to mammals at the concentration found in the venom. They inhibit the $Na^+K^+$ ATPase enzyme and are involved in the homeostasis of water and salts on the skin of toads. These steroids increase the blood pressure and stimulate the smooth muscles of some mammals even at diluted concentrations [Toledo, de R. C; Jared, C. 1995. Cutaneous granular glands and amphibian venoms. Comp. Biochem. Physiol. 111(1): 1-29].

The international patent application WO0214343 A1 (Novolan et al., 2002) describes the use of bufadienolides in a pharmaceutical preparation with immunomodulating activity, especially for immunosuppressant, antiinflammatory and/or, in the case of non-cardioactive bufadienolides, antiproliferative action. The document suggests a clinical protocol for the treatment of rheumatic pain in human beings, in which patients with inflammatory forms of rheumatism would receive injections of a bufadienolide, preferably proscillaridin A (0.1-3.0 mg), in the inflamed joints or tissues. However, no results of biological or clinical tests supporting the decrease of inflammation and pain are presented.

The objective of the present invention is to provide alternatives for the treatment or prevention of pain. In this sense, the present invention proposes the use of telocinobufagin as an effective and safe analgesic for the treatment or prevention of acute and chronic pains.

SUMMARY OF THE INVENTION

According to one incorporation of the present invention, it is described the use of telocinobufagin (Formula I), or its pharmaceutically acceptable derivatives, in the fabrication of a medication for the treatment or prevention of pain. More specifically, the present invention describes the use of telocinobufagin, or its pharmaceutically acceptable derivatives, for the treatment or prevention of acute and chronic pains in human beings or animals.

According to one incorporation of the present invention, it is described the use of a pharmaceutical composition comprising: (a) telocinobufagin or its pharmaceutically acceptable derivatives and (b) pharmaceutically acceptable excipients for the manufacture of a medication for treating disturbances or conditions in which pain predominates, including the acute and chronic pains (inflammatory, neuropathic and others).

According to another incorporation of the present invention, a method is provided for the treatment or prevention of acute and chronic pains comprising the administration of an effective amount of telocinobufagin or its pharmaceutically acceptable derivatives to human beings or animals.

According to another incorporation of the present invention, a method is provided to treat acute and chronic pains, which comprises the administration of a pharmaceutical composition comprising an effective amount of telocinobufagin, or its pharmaceutically acceptable derivatives, and pharmaceutically acceptable excipients to human beings or animals.

The present invention also describes a pharmaceutical composition comprising telocinobufagin, or its pharmaceutically acceptable derivatives, and pharmaceutically acceptable excipients.

The pharmaceutical composition of the present invention may be administered by the following routes: oral, sublingual, nasal, rectal, intragingival, intravenous, intramuscular, intraarticular, subcutaneous, inhalatory, transdermal, topical and spinal (subarachnoid and peridural). In particular, the oral route is preferred.

The term "animals", as used in the present invention, refers to domesticated animals, wild animals kept in captivity or not, and laboratory animals.

The term "effective amount", as used in the present invention, refers to an amount of telocinobufagin that provides the desired analgesic activity when administered according to a dose appropriate for each administration route.

The term "pharmaceutically acceptable excipients", as used in the present invention, refers to ingredients compatible with other ingredients, and that are not harmful to human beings or animals.

The term "pharmaceutically acceptable derivatives", as used in the present invention, refers to enantiomers, polymorphs, pseudopolymorphs (hydrates and solvates), pro-drugs, such as carbonates, carbamates, phosphates, phosphonates, glycosides, sulfates, sulfonates, ethers or esters.

The term "to treat", as used in the present invention, refers to revert, alleviate, inhibit, prevent, or diminish the progress of pain in human beings or animals. The term "treatment", as used in the present invention, refers to the act of treating as defined above as well as to prevention. The term "prevention", as used in the present invention, refers to the act of preventing, which is related to the term "preemptive analgesia". This term refers to the preventive treatment of pain, before its occurrence. Such procedure has been often used postoperatively, when the responsible doctor knows that pain will arise after cessation of anesthesia. It is also used in the treatment of cases of burns and chronic conditions, such as oncologic diseases, in which the doctor prescribes an analgesic regimen to be administered at fixed times and not only when the patient complains of pain. The aim of preemptive analgesia is to provide comfort to the patient, avoiding the onset of pain, and to prevent the occurrence of reflex hyperexcitability and neuronal sensitization in response to the peripheral nociceptive stimuli. Central sensitization, once established, is difficult to be suppressed, and may be associated with the appearance of neuropathic pain [Woof, C. J. 1983. Evidence for a central component of post-injury pain hypersensitivity. Nature, 686-688; Wall, P. D. 1988. The prevention of postoperative pain. Pain].

The term "to treat disturbances or conditions in which pain predominates, including acute and chronic pains", as used in the present invention, refers to pains caused by conditions selected from the following group: congenital or genetic disorders; traumas, surgeries or burns; infectious and/or parasitic disease; metabolic disease; inflammation; autoimmune disease; oncologic disease; intoxications; metabolic alterations and diseases; degenerative conditions (nervous system and other systems); dysfunctional conditions; psychological disturbances.

The disturbances or conditions in which pain predominates, including acute and chronic pains, as used in the present invention, are selected from the group, but not limited to, consisting of soft and peripheral tissue lesions, such as traumatic osteoarticular and muscular lesions, traumatic nervous system lesions, including radicular or medullar lesions, and mechanical lesions, due to radiation, surgical procedures, and thermal, chemical or electrical burns; pain of oncologic or non-oncologic origin with acute or chronic evolution, deriving from a somatic (for example, nociceptive), neuropathic or psychogenic mechanism; osteoarthritis, rheumatoid arthritis; musculoskeletal pain, particularly after trauma; orofacial pain, for example odontalgia; primary and secondary headaches, including migraine; abdominal pain; pain deriving from oncologic disease, including benign and malignant neoplasias, for example, cancer pain; postoperative pain; pain deriving from neurodegenerative diseases, including multiple sclerosis and amyotrophic lateral sclerosis; pain deriving from neuropathies associated with degenerative diseases, including diabetes and intervertebral disc hernia; pain deriving from metabolic alterations, including diabetes mellitus, hypotiroidism or hypertiroidism; pain deriving from repetitive strain injuries; pain deriving from congenital or genetic disorders; pain deriving from infectious or parasitic diseases, including Hansen's disease, herpes zoster, acquired immunodeficiency syndrome (AIDS), intoxications, including heavy metals; deafferentation pain, central pain, phantom limb pain, causalgia, myelopathic pain, complex regional pain syndrome, stump pain, reflex sympathetic dystrophy, postherpetic neuralgia, diabetic mononeuropathy, ischemic neuropathy, polyarteritis nodosa, post-radiotherapy pain, polyneuropathies, multiple mononeuritis, infectious and neurodegenerative myelopathies, toxic neuropathies, vasculitides and syringomyelia.

DESCRIPTION OF THE FIGURES

Descriptions of the Figures that accompany this detailed description are present below, for better understanding and illustration of the present invention.

DETAILED DESCRIPTION OF THE INVENTION

Figure 1:
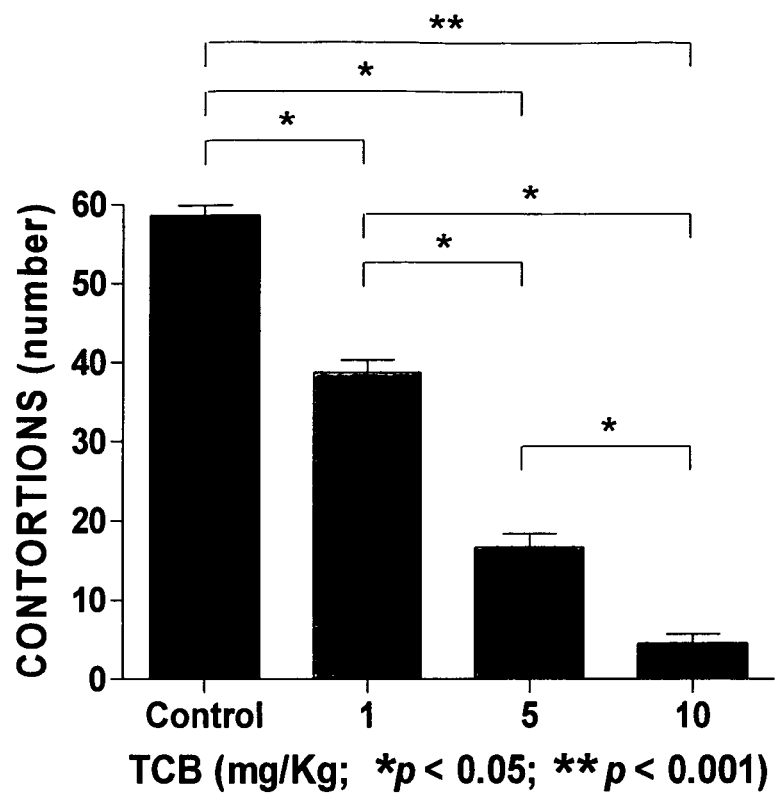
FIG. 1: Analgesic effects of oral telocinobufagin (dose/response curve), as determined by the abdominal contortion test in mice.

The present invention is directed to the use of telocinobufagin, or its pharmaceutically acceptable derivatives, in the manufacture of a medication for the treatment or prevention of pain. More specifically, the present invention describes the use of telocinobufagin for the treatment or prevention of acute and chronic pains in human beings or animals.

According to another incorporation of the present invention, a method is provided for the treatment or prevention of acute and chronic pains, comprising the administration of an effective amount of telocinobufagin, or its pharmaceutically acceptable derivatives, to human beings or animals.

According to another incorporation of the present invention, a method is provided to treat acute and chronic pains, which comprises the administration of a pharmaceutical composition comprising an effective amount of telocinobufagin, or its pharmaceutically acceptable derivatives, and pharmaceutically acceptable excipients, to human beings or animals.

According to the outcomes of the following tests, telocinobufagin is more potent than morphine, as demonstrated when the results are compared considering the molar masses of both substances, though without presenting the known side effects of opioids. Additionally, the results of the present invention show that the analgesic effects do not depend on the opioid system.

The results obtained for analgesia in response to both acute and chronic neuropathic pain were compared to several other conventional treatments of pain with drugs such as morphine sulfate, codeine phosphate, diclofenac sodium, dipyrone sodium, prednisone, amitriptyline chlorhydrate and carbamazepine, with greater efficacy of telocinobufagin.

The results of the present invention show that TCB does not have the same mechanism of action of opioids, since naloxone, a specific antagonist of morphine and its derivatives, was not capable of reverting its analgesic actions. Therefore, the treatment of acute and chronic pains with TCB is reached without causing the collateral effects usually observed with the conventional treatments with opioids, such as: constipation, physical and psychological dependence, respiratory depression, gastrointestinal lesions, nephrotoxicity, platelet aggregation inhibition, incidence of adverse effects associated with the central nervous system (blurred vision, dizziness, headache, mental confusion, nauseas, etc.).

The results of in vivo and in vitro tests also showed that telocinobufagin does not present signs of cardiac toxicity in preparations of isolated rat atrium.

Another incorporation of the present invention refers to a pharmaceutical composition containing an effective amount of telocinobufagin, or its pharmaceutically acceptable derivatives, and pharmaceutically acceptable excipients. A pharmaceutical composition according to the present invention comprising 0.1% to 99% p/p of telocinobufagin, or its pharmaceutically acceptable derivatives.

Telocinobufagin may be of natural or synthetic origin, and it may be presented in its several possible pharmaceutically acceptable forms of enantiomers, polymorphs, pseudopolymorphs (hydrates and solvates), pro-drugs such as carbonates, carbamates, phosphates, phosphonates, glycosides, sulfates, sulfonates, ethers or esters.

An example of derivatives appropriate to the invention is an ester formed from the reaction of a hydroxyl group of telocinobufagin (Examples: C3-OH, C5-OH or C14-OH) with carboxylic acids, for example, $C_n$—$CO_2H$ and $HO_2C$—$(CH_2)_n$—$CO_2H$ alkyl (where n is 1-10), and $CH_2$—$CO_2H$-phenyl. An example for the formation of ethers is the reaction of a hydroxyl group (Examples: C3-OH, C5-OH or C14-OH) with alkyl halides ($C_n$—X, where n is 1-10 and X is Cl, Br, I, F) and/or alkyl or aryl sulfonates.

The art specialist will recognize that telocinobufagin presents chirality and thus contains atoms that may be in a particular geometric and stereochemical configuration, originating configurational isomers and stereoisomers. All isomers and their mixture are included in the present invention.

According to the present invention, the administration of telocinobufagin, or pharmaceutical compositions containing this substance, may be performed by the following administration routes: oral, sublingual, nasal, rectal, intragingival, endovenous, intramuscular, intraarticular, subcutaneous, cutaneous (for example, patch or transdermal patch), inhalatory, transdermal, topical or spinal (subarachnoid and peridural), not being limited to these. In particular, the oral route is preferred.

The pharmaceutically acceptable excipients are selected according to the final presentation of the composition of the present invention, which may be in the form of capsules or tablets for oral administration, solutions for nasal administration, injectable solutions for intramuscular, endovenous, cutaneous or subcutaneous administration, and lotion, cream or ointment for topical administration.

Methods for the preparation of several pharmaceutical compositions are well known, or will be recognized in the light of the present invention, by the art specialist in pharmaceutical technology. For example, see *Remington's Pharmaceutical Sciences*, 18th ed. (1990).

The following examples are merely illustrative, and should only be used for a better understanding of the constant developments in the present invention, although they should not be used with the intention of limiting the described objects.

In Vivo Assays for Acute Pain:

The following in vivo assays for acute pain were used: contortion assay, formalin assay, hot plate assay and tail flick assay.

The different assays were performed for several doses of oral TBC, using at least 6 animals for each dose. The statistical analysis of the results was done by ANOVA followed by the TUKEY's test (p<0.05).

Administration route: Telocinobufagin was administered by the oral route, dissolved in 40% dimethyl sulfoxide (DMSO) in water. The animals were maintained in a 12-hour fasting period before the beginning of the experiments. The other drugs, morphine sulfate, codeine phosphate, diclofenac sodium, dipyrone sodium, prednisone, amitriptyline chlorhydrate and carbamazepine, were administered by the intraperitoneal route (i.p.).

Animals: Approximately 500 male Swiss mice (*Mus musculus*) were used.

EXAMPLE 1

Contortion Assay

Contortion assay in mice: Distinction between central and peripheral analgesic activities. This assay is based on the intraperitoneal administration of substances that irritate the serous membrane, for example, acetic acid, provoking a stereotyped behavior in the mouse, which is characterized mainly by abdominal contractions, accompanied by stretching of the hindpaws. This behavior is considered of reflected origin and is indicative of visceral pain, similar to that associated with peritonitis. Although this assay does not have great specificity, it is extremely sensitive, being one of the most used assays for the screening of new analgesics. As the contortion assay permits evaluating the antinociceptive activity of substances that act at both central and peripheral levels, when it is associated with a specific central action assay (e.g.: hot plate assay), it is possible to demonstrate if the level of action of a certain drug is central and peripheral, or exclusively peripheral, or exclusively central. The control groups received orally the same volume of vehicle (10 mL/kg) used to dilute the compounds under analysis 1 hour before the assay, while the treated groups received, under the same conditions, the crescent doses of the tested substances. Fifty-five minutes after oral administration of the drugs and thereafter 5 minutes after intraperitoneal injection of 0.6% acetic acid, the animals were observed by measuring, cumulatively, the number of abdominal contortions during a period of 20 minutes. The antinociceptive activity was determined based on the inhibition of the number of contortions of the treated animals compared to the number of contortions of the animals of the control group. The results are presented in FIGS. 1-3.

FIG. 1 presents the analgesic effects of oral telocinobufagin (dose/response curve), as determined by the abdominal contortion assay in mice. This Figure demonstrates that telocinobufagin had significant antinociceptive effects in the referred assay, even blocking, at a dose of 10 mg/kg, nearly 90% of the contortions compared to the control group (p<0.001).

Figure 2:
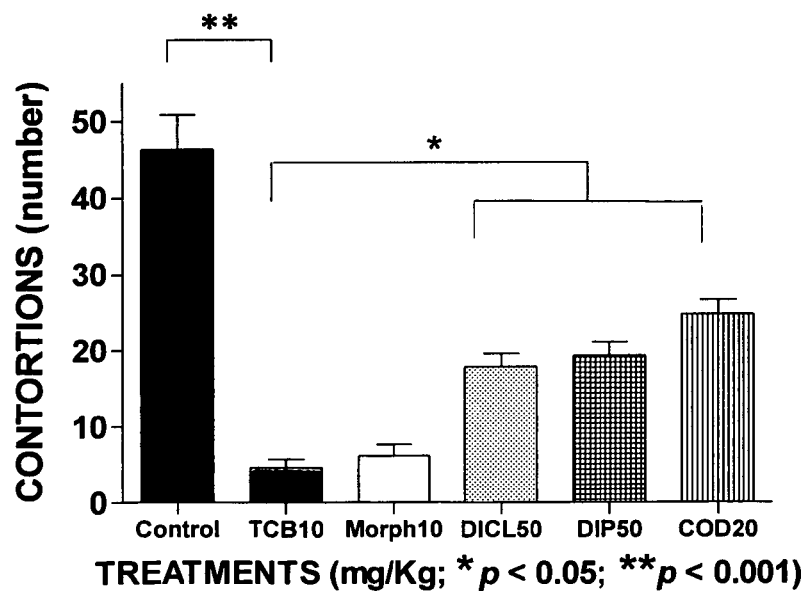
FIG. 2: Comparison of the effects of telocinobufagin (10 mg/kg, oral), morphine sulfate "Morph" (10 mg/kg, i.p.), diclofenac sodium "DICL" (50 mg/kg, i.p.), dipyrone sodium, "DIP" (50 mg/kg, i.p.) and codeine phosphate "COD" (20 mg/kg, i.p.), as determined by the abdominal contortion test in mice.

FIG. 2 compares the effects of telocinobufagin (10 mg/kg, oral) to those of morphine sulfate "Morph" (10 mg/kg, i.p.), diclofenac sodium "DICL" (50 mg/kg, i.p.), dipyrone sodium "DIP" (50 mg/kg, i.p.) and codeine phosphate "COD" (20 mg/kg, i.p.), as determined by the abdominal contortion assay in mice. This Figure demonstrates that the antinociceptive effect, mol to mol, of telocinobufagin administered orally was nearly 40% greater than that of morphine administered intraperitoneally and pretty much superior to the effects of the other analgesics used in the referred assay, which were also administered intraperitoneally (p<0.05).

Figure 3:
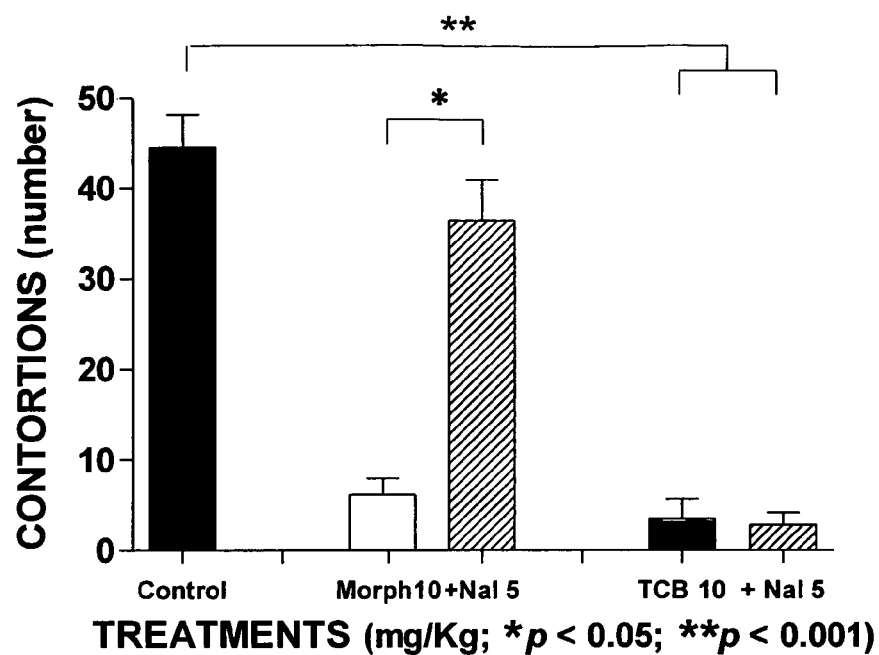
FIG. 3: Effects of naloxone (5 mg/kg, i.p.) on the analgesic action of telocinobufagin (10 mg/kg, oral), as determined by the abdominal contortion test in mice.

FIG. 3 presents the effects of naloxone (5 mg/kg) on the analgesic action of telocinobufagin (10 mg/kg), as determined by the abdominal contortion assay in mice. This Figure demonstrates that naloxone, i.p., at a dose of 5 mg/kg blocked the effects of morphine, i.p., at dose of 10 mg/kg (p<0.05), but did not block the analgesic effects of telocinobufagin administered orally at a dose of 10 mg/kg.

EXAMPLE 2

Formalin Assay

Evaluation of neurogenic and inflammatory acute pains. The intraplantar 4% formalin injection assay induces in the animal reactions of licking or contracting the paws. This assay permits evaluating two types of pain: one of neurogenic origin, as a result of the direct stimulation of the nociceptive neurons, which is observed in the first 5 minutes after formalin administration, and another of inflammatory origin, characterized by the release of inflammatory mediators, which is observed between 15 and 30 minutes after the formalin injection and represents the tonic response to pain. This assay was undertaken at room temperature (24-25° C.) and in the absence of experimental factors that can affect the peripheral blood flow due to the great sensitivity of the response in the second phase (delayed). The control groups received orally the same volume of vehicle (10 mL/kg) used to dilute the compounds under analysis 1 hour before the assay, while the treated groups received, under the same conditions, the crescent doses of the substances to be tested. The antinociceptive activity was then determined based on the decrease of the cumulative time of paw licking or contraction in the treated animals compared to the same responses of the animals of the control group.

The results of the formalin assay are displayed in FIGS. 4-9.

Figure 4:
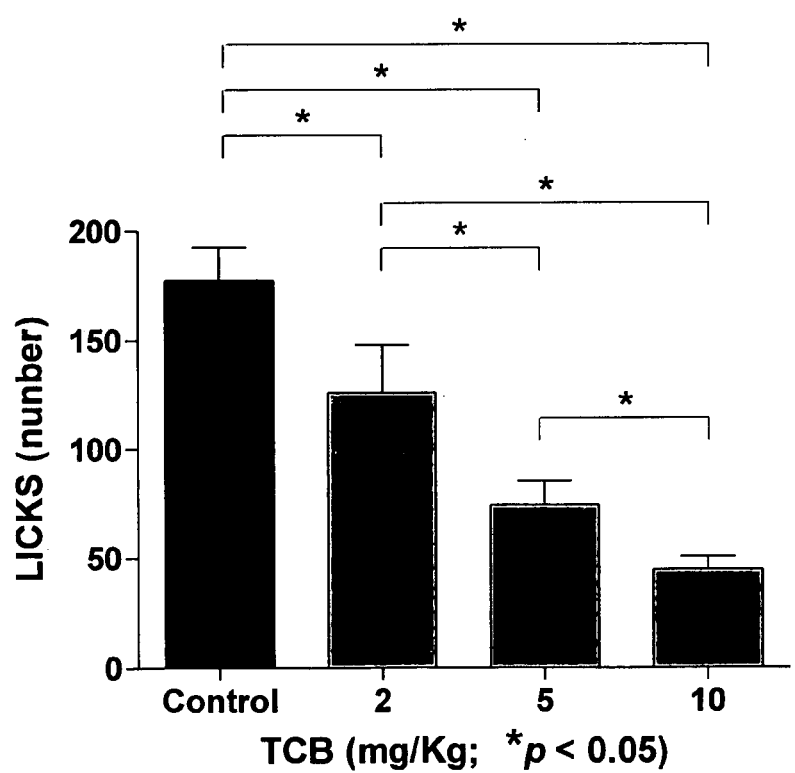
FIG. 4: Analgesic effects of oral telocinobufagin (dose/response curve), in phase 1 of the formalin assay in mice.

FIG. 4 presents the analgesic effects of telocinobufagin (dose/response curve), administered by the oral route, in the phase 1 of the formalin assay in mice. This Figure shows that telocinobufagin presented significant antinociceptive effects in the referred test, even blocking, at a dose of 10 mg/kg, nearly 80% of the licks compared to the control group ($p<0.005$).

Figure 5:
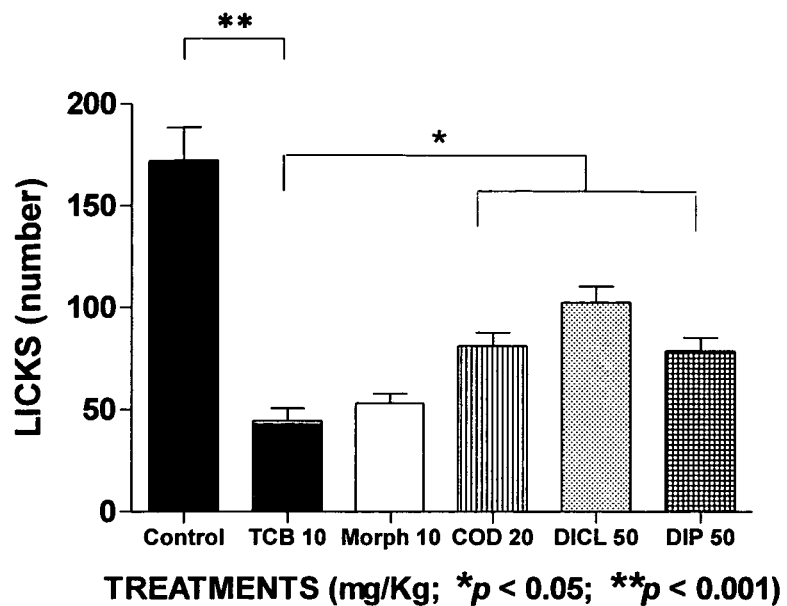
FIG. 5: Comparison of the effects of telocinobufagin (10 mg/kg, oral), morphine sulfate "Morph" (10 mg/kg, i.p.), diclofenac sodium "DICL" (50 mg/kg, i.p.), dipyrone sodium "DIP" (50 mg/kg, i.p.) and codeine phosphate "COD" (20 mg/kg, i.p.), in phase 1 of the 4% formalin test in mice.

FIG. 5 compares the effects of telocinobufagin (10 mg/kg, oral) to those of morphine sulfate "Morph" (10 mg/kg, i.p.), diclofenac sodium "DICL" (50 mg/kg, i.p.), dipyrone sodium "DIP" (50 mg/kg, i.p.) and codeine phosphate "COD" (20 mg/kg, i.p.), in the phase 1 of the 4% formalin assay in mice. This Figure demonstrates that the antinociceptive effect, mol to mol, of telocinobufagin administered orally was nearly 40% greater than that of morphine administered intraperitoneally and pretty much superior to that of the other analgesics used in the referred assay ($p<0.05$).

Figure 6:
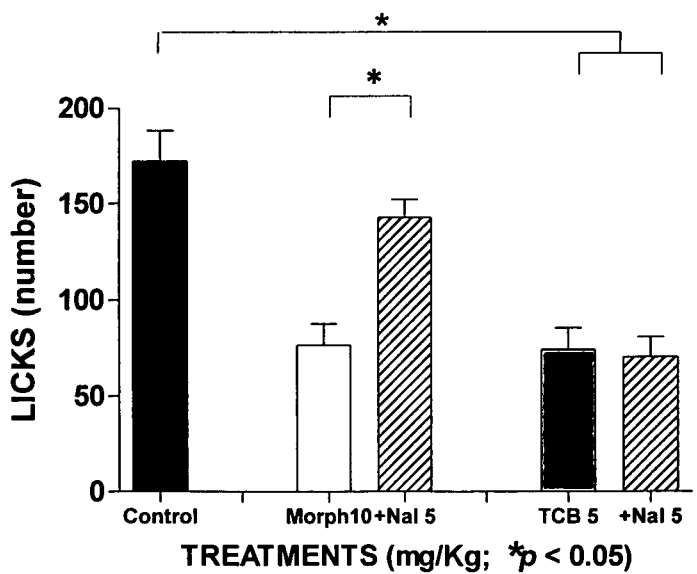
FIG. 6: Effects of naloxone (5 mg/kg) on the analgesic action of telocinobufagin (5 mg/kg), in phase 1 of the formalin assay.

FIG. 6 presents the effects of naloxone (5 mg/kg) on the analgesic action of telocinobufagin (5 mg/kg), in the phase 1 of the formalin assay. This Figure shows that naloxone at a dose of 5 mg/kg, i.p., blocked the effects of morphine, at a dose of 10 mg/kg ($p<0.05$), but did not block the analgesic effects of telocinobufagin administered orally at a dose of 5 mg/kg.

Figure 7:
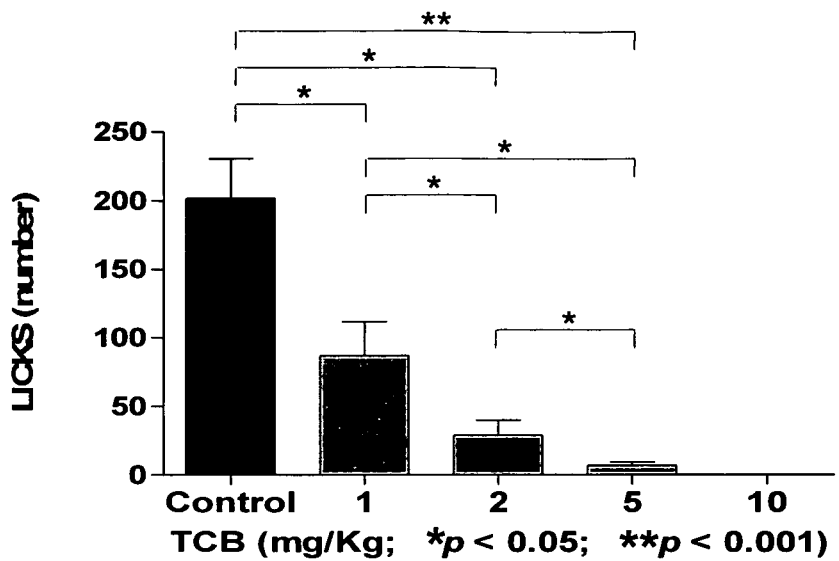
FIG. 7: Analgesic effects of oral telocinobufagin (dose/response curve) in phase 2 of the formalin assay.

FIG. 7 presents the analgesic effects of telocinobufagin administered by the route oral (dose/response curve) in the phase 2 of the formalin assay. This Figure demonstrates that telocinobufagin presented significant antinociceptive effects in the referred assay, even blocking, at a dose of 10 mg/kg, nearly 100% of the licks compared to the control group ($p<0.0001$).

Figure 8:
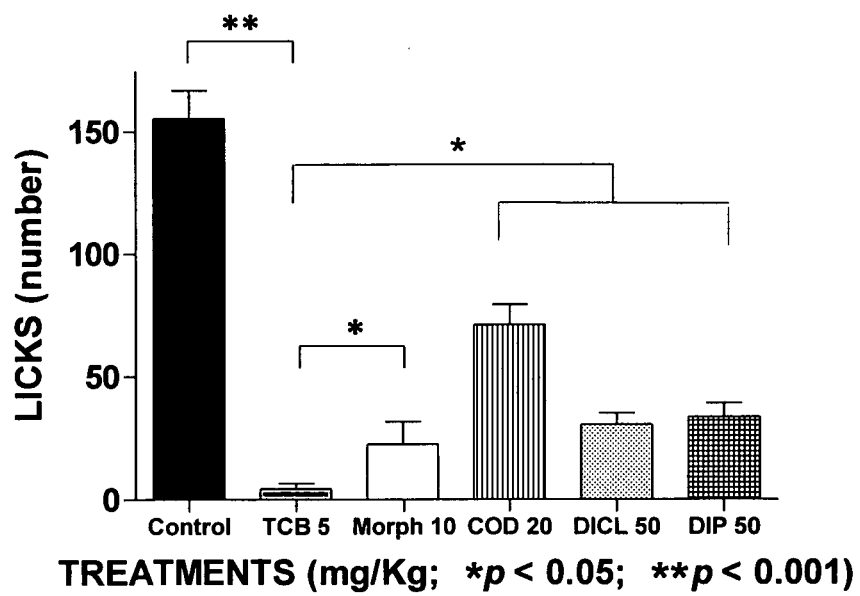
FIG. 8: Comparison of the effects of telocinobufagin (5 mg/kg, oral), morphine sulfate "Morph" (10 mg/kg, i.p.), diclofenac sodium "DICL" (50 mg/kg, i.p.), dipyrone sodium "DIP" (50 mg/kg, i.p.) and codeine phosphate "COD" (20 mg/kg, i.p.), in phase 2 of the formalin assay.

FIG. 8 compares the effects of telocinobufagin (5 mg/kg, oral) to those of morphine sulfate "Morph" (10 mg/kg, i.p.), diclofenac sodium "DICL" (50 mg/kg, i.p.), dipyrone sodium "DIP" (50 mg/kg, i.p.) and codeine phosphate "COD" (20 mg/kg, i.p.), in the phase 2 of the formalin assay. This Figure demonstrates that the antinociceptive effect, mol to mol, of telocinobufagin administered orally was nearly 58% greater than that of morphine administered intraperitoneally and pretty much superior to that of the other analgesics used in the referred assay ($p<0.05$).

Figure 9:
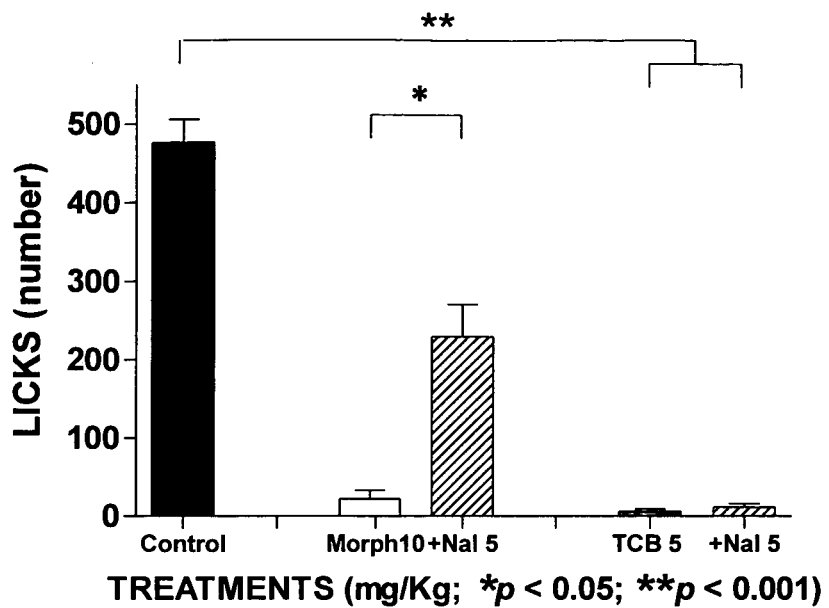
FIG. 9: Effects of naloxone (5 mg/kg) on the analgesic action of telocinobufagin (5 mg/kg) in phase 2 of the formalin assay.

FIG. 9 presents the effects of naloxone (5 mg/kg) on the analgesic action of telocinobufagin (5 mg/kg) in the phase 2 of the formalin assay. This Figure demonstrates that naloxone, i.p., at a dose of 5 mg/kg blocked the effects of morphine, administered at a dose of 10 mg/kg ($p<0.05$), but did not block the analgesic effects of telocinobufagin administered orally at a dose of 5 mg/kg.

EXAMPLE 3

Hot Plate Assay

Determination of the central analgesic activity. This assay consists in disposing the animals on a hot plate ($52\pm0.5°$ C.) and observing how long they take to manifest a response, particularly reacting by licking their paws or jumping. Both reactions are considered as integrated supraspinal (cerebral) responses. The control groups received orally the same volume of vehicle (10 mL/kg) used to dilute the compounds under analysis 1 hour before the assay, while the treated groups received, under the same conditions, the crescent doses of the substances to be tested. The antinociceptive activity was determined based on the increase of the latency time for the treated animals to lick their paws or jump compared to the same responses of the animals of the control group. The results are displayed in FIGS. 10 and 11.

Figure 10:
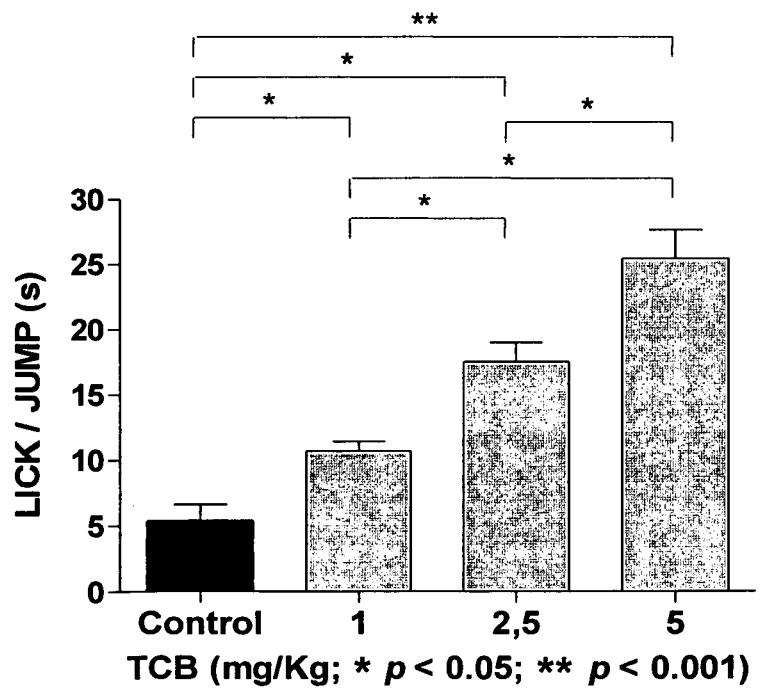
FIG. 10: Analgesic effects of oral telocinobufagin (1 mg/kg, 2.5 mg/kg and 5 mg/kg) in the hot plate assay.

FIG. 10 presents a dose/response curve of the analgesic effects of oral telocinobufagin (1 mg/kg, 2.5 mg/kg and 5 mg/kg) in the hot plate assay. This Figure demonstrates that telocinobufagin presented significant antinociceptive effects in the referred assay, even increasing the response by approximately 450% at the dose of mg/kg (oral), compared to control group ($p<0.001$).

Figure 11:
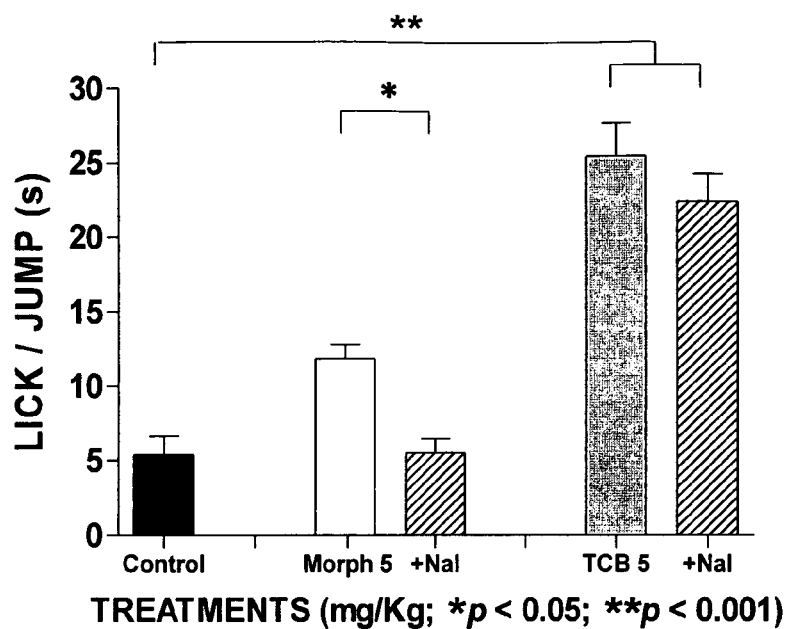
FIG. 11: Effects of naloxone (5 mg/kg) on the analgesic action of telocinobufagin (5 mg/kg) in the hot plate assay.

FIG. 11 presents the effects of naloxone (5 mg/kg) on the analgesic action of telocinobufagin (5 mg/kg) in the hot plate assay. This Figure shows that naloxone at a dose of 5 mg/kg, i.p., blocked the effects of morphine, at a dose of mg/kg ($p<0.05$), but did not block the analgesic effects of telocinobufagin administered orally at a dose of 5 mg/kg.

EXAMPLE 4

Tail Flick Assay

Determination of the analgesic activity at the medullar level. We chose the variant of the assay that consists in the application of thermal radiation through a filament that is heated in few seconds up to 70° C., in contact with a small surface of the animal tail. This thermal stimulus provokes a tail flick reaction in the control animals by means of a rapid and vigorous reflex movement of spinal origin, after a period that ranges from 2 to 10 seconds. The increase in the tail flick time is interpreted as an analgesic action. The control groups received orally the same volume of vehicle (10 mL/kg) used to dilute the compounds under analysis 1 hour before the assay, while the treated groups received, under the same conditions, the crescent doses of the substances to be tested. The antinociceptive activity was determined based on the increase of the latency time for the tail flick reaction in the treated animals compared to same responses of the animals of the control group. The results of this assay are displayed in FIGS. 12 and 13.

Figure 12:
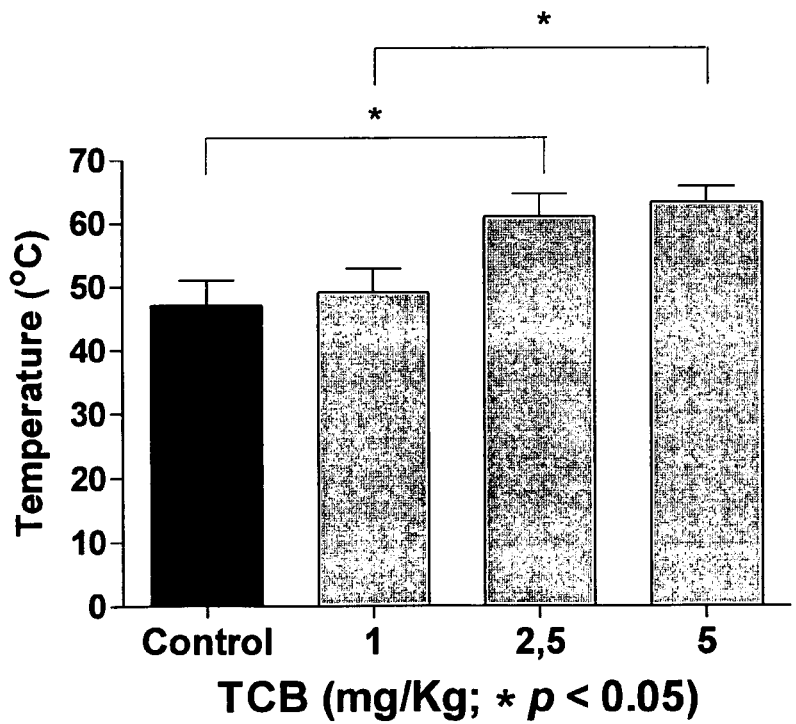
FIG. 12: Effects of telocinobufagin (1 mg/kg, 2.5 mg/kg and 5 mg/kg) in the tail flick assay.

FIG. 12 presents the effects of telocinobufagin (1 mg/kg, 2.5 mg/kg and 5 mg/kg) in the tail flick assay. This Figure demonstrates that telocinobufagin at the doses of 2.5 and 5 mg/kg presented significant antinociceptive effects in the referred assay ($p<0.05$).

Figure 13:
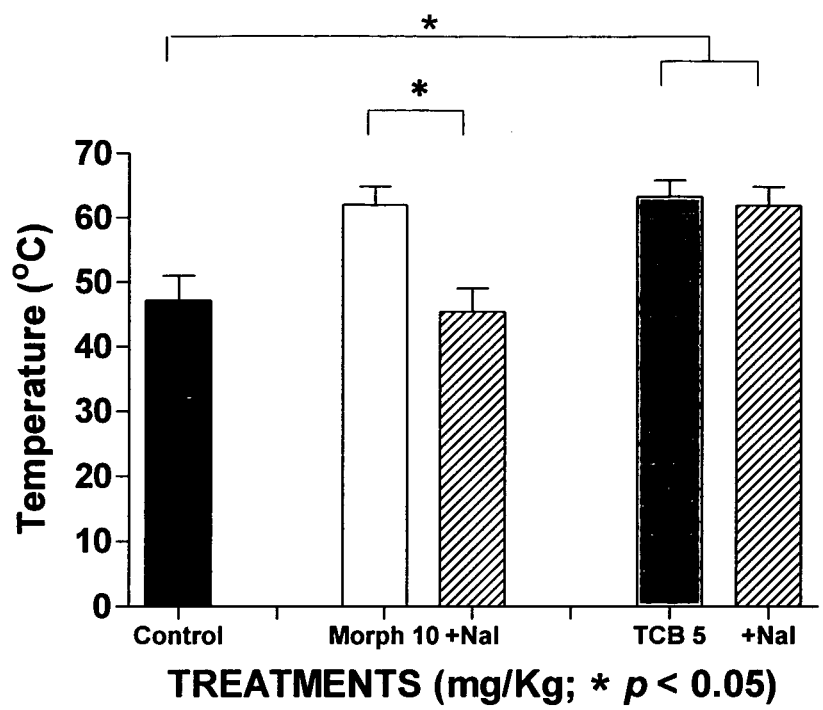
FIG. 13: Effects of naloxone (5 mg/kg) on the analgesic action of telocinobufagin (5 mg/kg) in the tail flick assay. For the Figures below: RP=right paw before the surgical ligature of the sciatic nerve; RPtest=right paw after the surgical ligature of the sciatic nerve.

FIG. 13 presents the effects of naloxone (5 mg/kg) on the analgesic action of telocinobufagin (5 mg/kg) in the tail flick assay. This Figure demonstrates that naloxone at the dose of 5 mg/kg, i.p., blocked the effects of morphine, at a dose of 10 mg/kg ($p<0.05$), but did not block the analgesic effects of telocinobufagin administered orally at a dose of 5 mg/kg.

In Vivo Assays for Chronic Pain:

EXAMPLE 5

Chronic Constrictive Injury (CCI) Model

Recently, several animal models of neuropathic pain have been developed in rats. According to the method described by Bennett [Bennett. G. J; Xie, Y. K. 1998. A peripheral mononeuropathy in rat that produces disorders of pain sensation like those seen in man. Pain, 33: 87-107], under anesthesia, the rat is positioned in the ventral decubitus position and an incision is done on the skin along the thigh. The fascia between the gluteus muscle and the femoral biceps muscle is dissected and the right common sciatic nerve is exposed at the median level of the thigh. Close to this trifurcation, the nerve is carefully dissected from the surrounding tissue for a distance of approximately 8 mm, where the assay is performed.

In this experimental model of neuropathic pain were measured: a) Allodynia: pain in response to non-injurious stimuli; b) Hyperalgesia: exaggerated pain in response to injurious stimuli. Peripheral neuropathy was produced by placing loosely constrictive ligatures around the sciatic nerve (Chronic constrictive injury, CCI) according to the method described by Bennett and Xie (1988). Adult rats were anesthetized with sodium pentobarbital (40 mg/kg, i.p.) and had their bilateral sciatic nerves were exposed by dissection of the femoral biceps muscle. In one side, four chromic gut constrictive ligatures (4-0), approximately 1 mm spaced, were loosely tied around the nerve. In the contralateral side, all surgical steps were performed, such as exposure and handling of the nerve, but no ligatures were placed. To minimize the technique variations, all procedures were undertaken by a single operator. A single antibiotic dose (Ampicillin 8,000 u/rat, Sigma, St Louis, Mo.) was administered at the end of the surgical phase. Before the beginning of the assays, a period of approximately 5 days was established for recovery of the animals.

Determination of Allodynia. The method described by Chaplan was used, using von Frey device [Chaplan, S. R., Bach, F. W., Pogrel, J. W., Chung, J. M., Yaksh, T. L. 1994. Quantitative assessment of tactile allodynia in the rat paw. *J Neurosci Methods*. 53:55-63]. The response time to the tactile stimulus applied to the rat hindpaw was measured.

Determination of Hyperalgesia. The Randall & Selitto's rat paw pressure assay was used [Randall, L. O., Selitto, J. J. 1957. A method for measurement of analgesic activity on inflamed tissue. Arch Int Pharmacodyn Ther 111: 409-419]: the force was applied continuously on the dorsum of the paw (16 g/s) and was interrupted upon its removal. The results of the assays performed by the chronic constrictive injury model are displayed in FIGS. 14-25.

Figure 14:
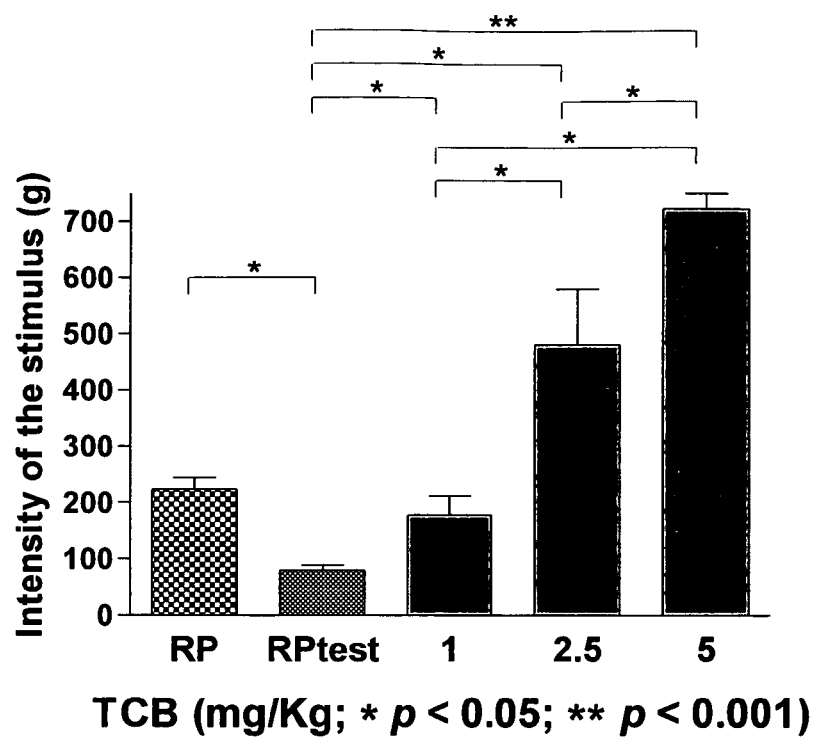
FIGS. 14 and 15: Effects of telocinobufagin (dose/response curve) administered by the intraperitoneal (14) and oral (15) routes, respectively, on hyperalgesia.
Figure 15:
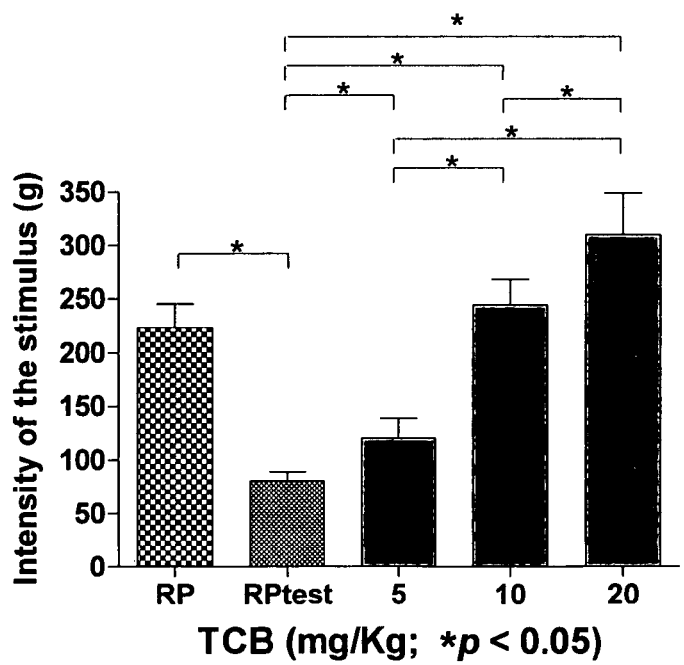

FIGS. 14 and 15 present the effects of intraperitoneal and oral telocinobufagin (dose/response curve), respectively, on hyperalgesia. These Figures demonstrate that telocinobufagin presented significant antinociceptive effects in the referred assays, even increasing the responses approximately 9 and 3.9 times compared to the control group (RPtest), when administered by the intraperitoneal (5 mg/kg) ($p<0.001$) and oral (20 mg/kg) ($p<0.05$) routes, respectively.

Figure 16:
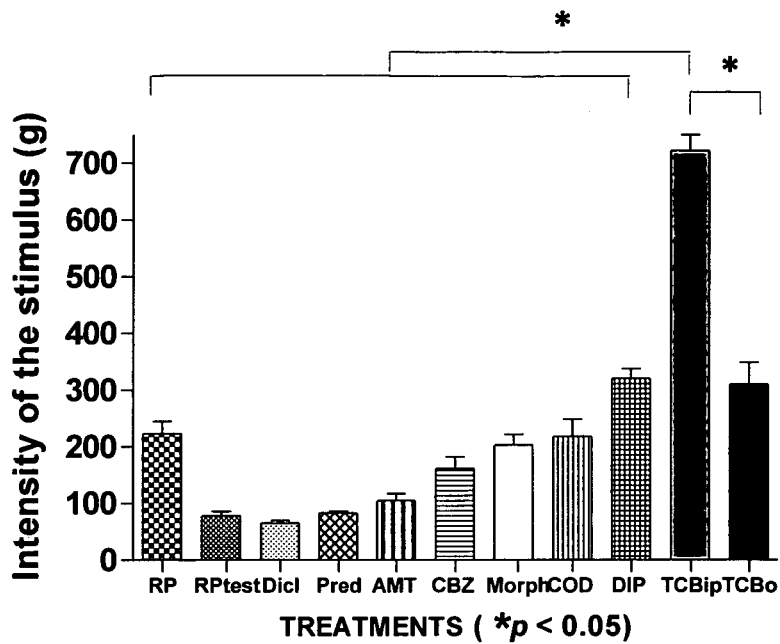
FIG. 16: Comparison of the analgesic effects of intraperitoneal (5 mg/kg) and oral (20 mg/kg) telocinobufagin with the following analgesics on hyperalgesia: diclofenac sodium "DICL" (50 mg/kg, i.p.), morphine sulfate "Morph" (10 mg/kg, i.p.), codeine phosphate "COD" (30 mg/kg, i.p.), dipyrone sodium "DIP" (300 mg/kg, i.p.), amitriptyline chlorhydrate "AMT" (30 mg/kg), carbamazepine "CBZ" (60 mg/kg) and prednisone "PRED" (10 mg/kg).

FIG. 16 compares the analgesic effects of telocinobufagin (5 mg/kg, i.p.; 20 mg/kg, oral) to those of the following analgesics on hyperalgesia: diclofenac sodium "DICL" (50 mg/kg, i.p.), morphine sulfate "Morph" (10 mg/kg, i.p.), codeine phosphate "COD" (30 mg/kg, i.p.), dipyrone sodium "DIP" (300 mg/kg, i.p.), amitriptyline chlorhydrate "AMT" (30 mg/kg), carbamazepine "CBZ" (60 mg/Kg) and prednisone "PRED" (10 mg/kg). This Figure demonstrates that the antinociceptive effect, mol to mol, of telocinobufagin administered orally and intraperitoneally was approximately 900% greater than that of morphine administered intraperitoneally, and also pretty much superior to that of the other analgesics administered by the same route in the referred assay ($p<0.05$). The effect of oral TBC, mol to mol, was similar to that of morphine administered intraperitoneally.

Figure 17:
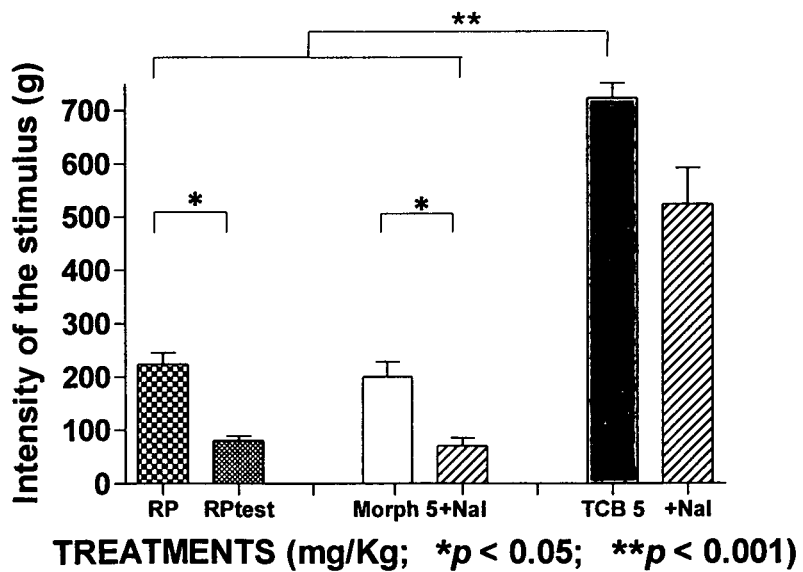
FIG. 17: Effects of naloxone (5 mg/kg, i.p.) on the analgesic action of telocinobufagin (5 mg/kg) in the hyperalgesia assay.

FIG. 17 presents the effects of naloxone (5 mg/kg, i.p.) on the analgesic action of telocinobufagin (5 mg/kg) in the hyperalgesia assay. This Figure shows that naloxone at the dose of 5 mg/kg, i.p., blocked the effects of morphine, at the dose of 10 mg/kg ($p<0.05$), but did not block significantly the analgesic effects of telocinobufagin administered intraperitoneally at the dose of 5 mg/kg.

Figure 18:
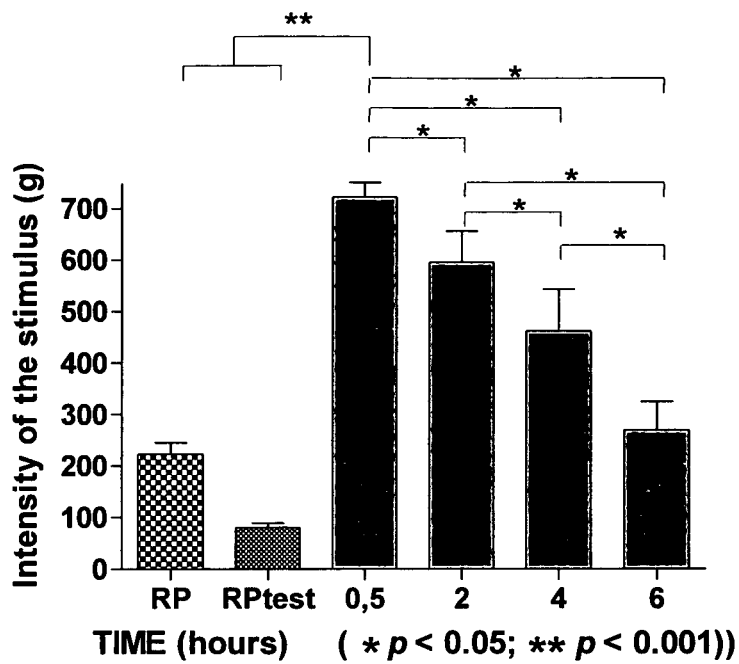
FIGS. 18 and 19: Duration of the analgesic effects of intraperitoneal (5 mg/kg) (18) and oral (20 mg/kg) (19) telocinobufagin, respectively, on hyperalgesia.
Figure 19:
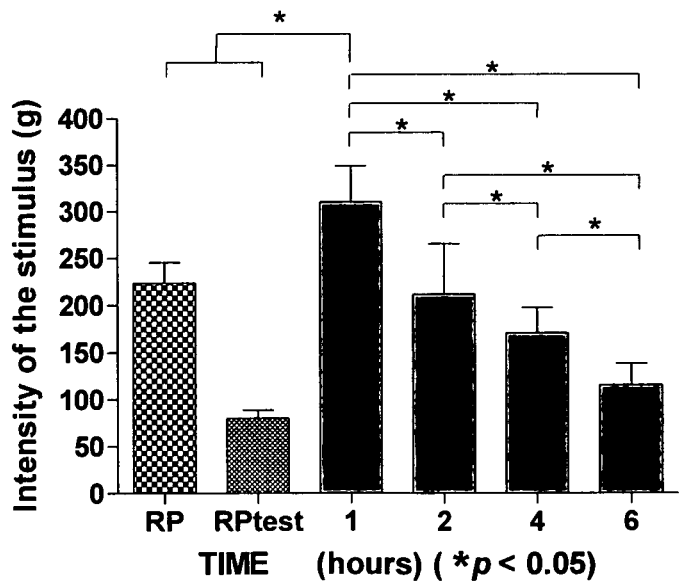

FIGS. 18 and 19 present the duration of the analgesic effects of intraperitoneal and oral telocinobufagin on hyperalgesia, respectively. These Figures show that the analgesic effects of telocinobufagin administered by the intraperitoneal (5 mg/kg) and oral (20 mg/kg) routes on hyperalgesia lasted around 6 hours, with an estimated half-life of 3 hours ($p<0.05$).

Figure 20:
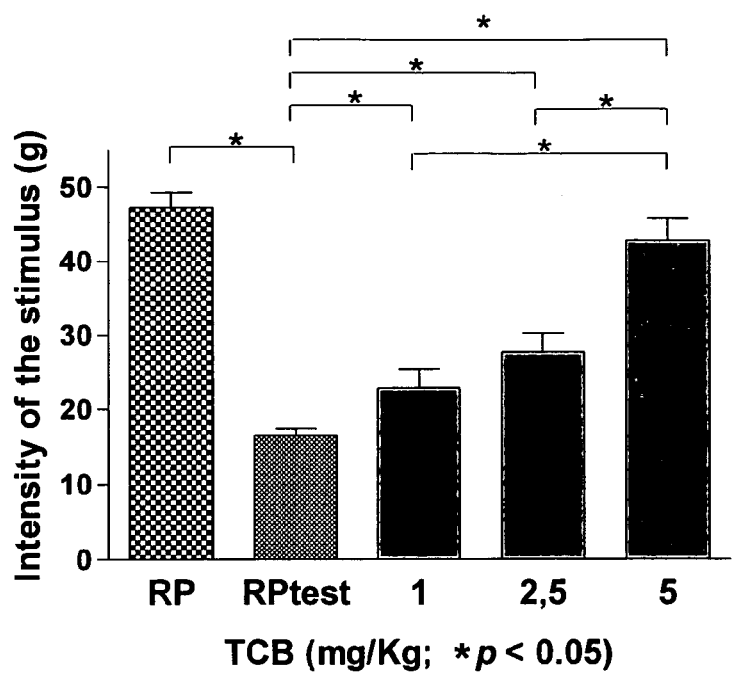
FIGS. 20 and 21: Effects of telocinobufagin (dose/response curve) administered by the intraperitoneal (20) and oral (21) routes, respectively, on allodynia.
Figure 21:
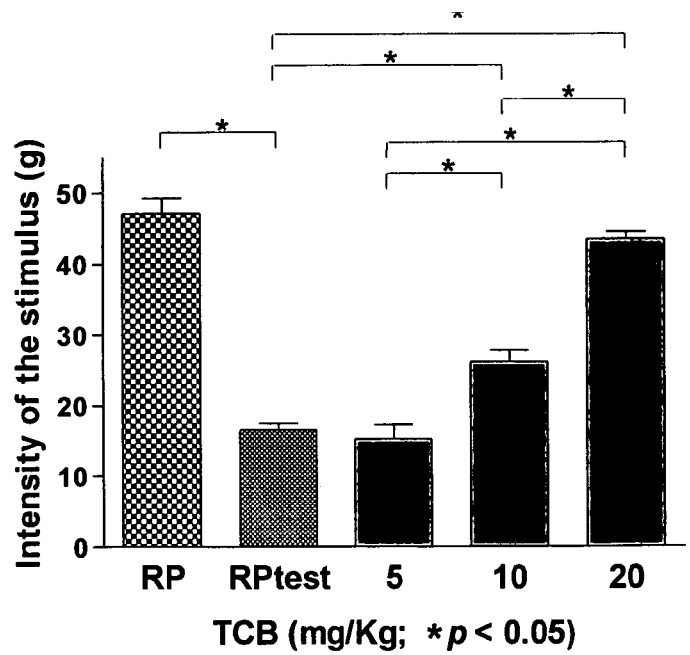

FIGS. 20 and 21 present the effects of intraperitoneal and oral telocinobufagin on allodynia, respectively. These Figures demonstrate that telocinobufagin presented significant antinociceptive effects in the referred assay, even blocking completely the allodynia at the doses of 5 mg/kg (i.p.) and 20 mg/kg (oral) ($p<0.05$).

Figure 22:
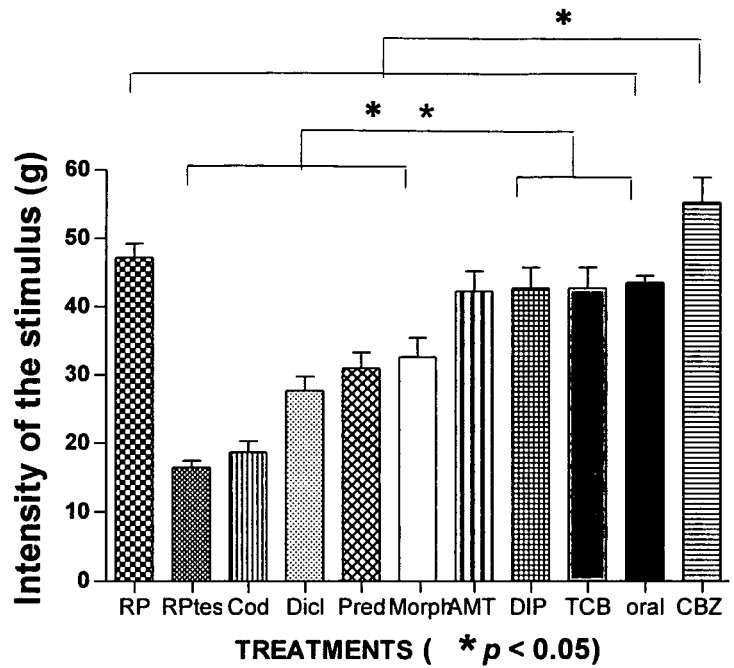
FIG. 22: Comparison of the analgesic effects of intraperitoneal (5 mg/kg) and oral (20 mg/kg) telocinobufagin with the following analgesics on allodynia: diclofenac sodium "DICL" (50 mg/kg, i.p.), morphine sulfate "Morph" (10 mg/kg, i.p.), codeine phosphate "COD" (30 mg/kg, i.p.), dipyrone sodium "DIP" (300 mg/kg, i.p.), amitriptyline chlorhydrate "AMT" (30 mg/kg) and carbamazepine "CBZ" (60 mg/kg) and prednisone "PRED" (10 mg/kg).

FIG. 22 compares the analgesic effects of telocinobufagin (5 mg/kg, i.p.; 20 mg/kg, oral) to those of the following analgesics on allodynia: diclofenac sodium "DICL" (50 mg/kg, i.p.), morphine sulfate "Morph" (10 mg/kg, i.p.), codeine phosphate "COD" (30 mg/kg, i.p.), dipyrone sodium "DIP" (300 mg/kg, i.p.), amitriptyline chlorhydrate "AMT" (30 mg/kg), carbamazepine "CBZ" (60 mg/kg) and prednisone "PRED" (10 mg/kg). This Figure shows that oral and intraperitoneal telocinobufagin blocked completely the allodynia at the doses of 5 mg/kg (i.p.) and 20 mg/kg (oral) ($p<0.05$), which are lower doses than those of amitriptyline chlorhydrate (30 mg/kg, i.p.) and carbamazepine (60 mg/kg, i.p.) ($p<0.05$). The results showed that both intraperitoneal and oral TBC, reverted completely the allodynia (compared to RP), while intraperitoneal morphine reverted only nearly 50% of the allodynia (compared to RP).

Figure 23:
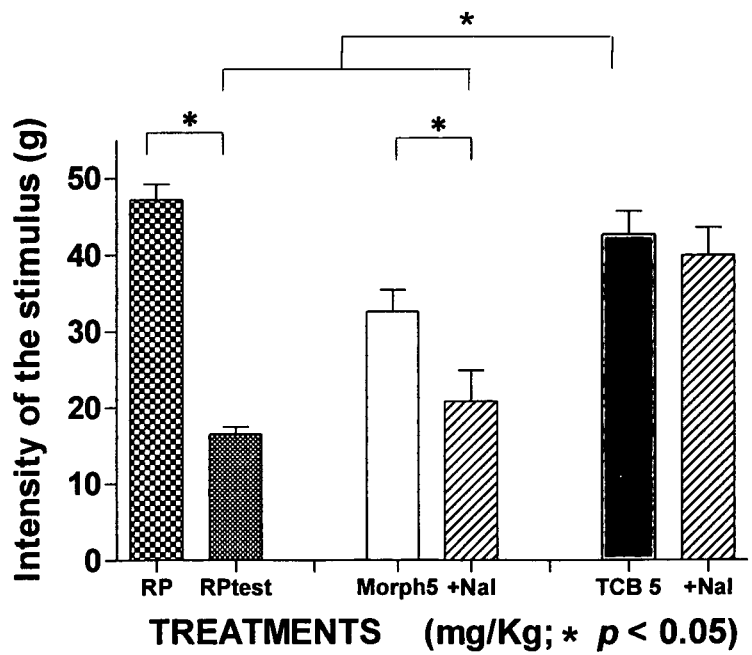
FIG. 23: Effects of naloxone (5 mg/kg, i.p.) on the analgesic action of telocinobufagin (5 mg/kg, i.p.) in the allodynia assay.

FIG. 23 presents the effects of naloxone (5 mg/kg, i.p.) on the analgesic action of telocinobufagin (5 mg/kg, i.p.) in the allodynia assay. This Figure demonstrates that naloxone at the dose of 5 mg/kg, i.p., blocked the effects of morphine, at the dose of 10 mg/kg ($p<0.05$), but did not block significantly the analgesic effects of intraperitoneal telocinobufagin at the dose of 5 mg/kg.

Figure 24:
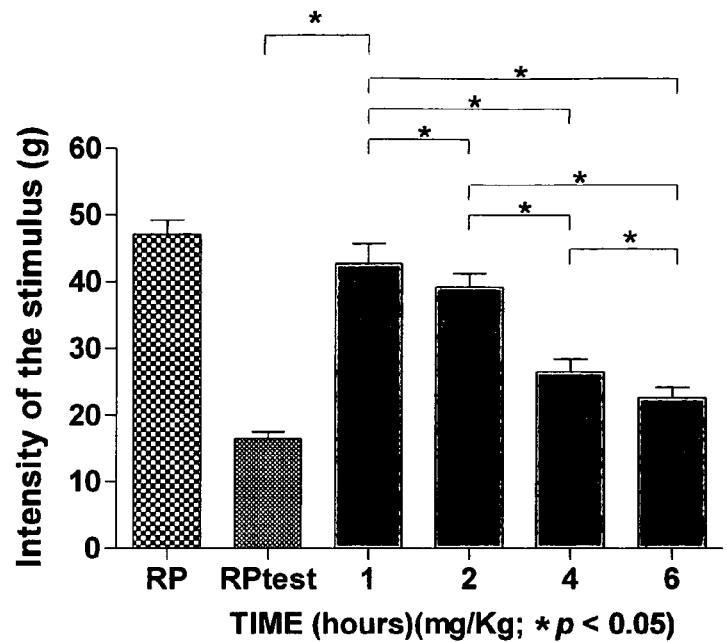
FIGS. 24 and 25: Duration of the analgesic effects of intraperitoneal (5 mg/kg) (24) and oral (20 mg/kg) (25) telocinobufagin, respectively, on allodynia.
Figure 25:
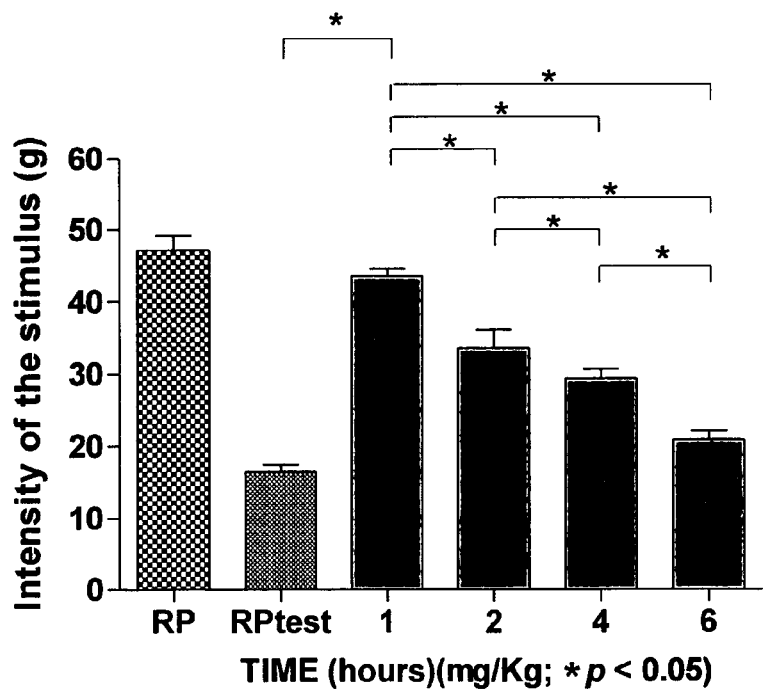

FIGS. 24 and 25 present the duration of the analgesic effects of intraperitoneal and oral telocinobufagin on allodynia, respectively. These Figures show that the analgesic effects of telocinobufagin administered by the intraperitoneal (5 mg/kg) and oral (20 mg/kg) routes on allodynia lasted around 6 hours, with an estimated half-life of 3 hours ($p<0.05$).

In Vivo Assays to Evaluate Cardiotoxicity:

EXAMPLE 6

Effect of Telocinobufagin on the Inotropism of Isolated Rat Atrium

In order to investigate the possible deleterious effects of telocinobufagin on the heart, an isolated rat atrium model was initially used to evaluate the cardiac contractile force (inotropism). The left atrium of rats was used to assess the inotropic activity. The data were expressed as contraction force (g of tension), and were compared to the results obtained with bupivacaine.

The application of square pulses (5 V, 5 ms, 2 Hz) in the left atrium with frequency of 120 bpm was sufficient to produce a cardiac contraction force of 0.63±0.09 g of tension. The response in the contractility did not suffer significant alterations when the conditions to which the left atrium was subjected in the superperfusion medium were maintained. The results of these assays are demonstrated in FIGS. 26-28.

Figure 26:
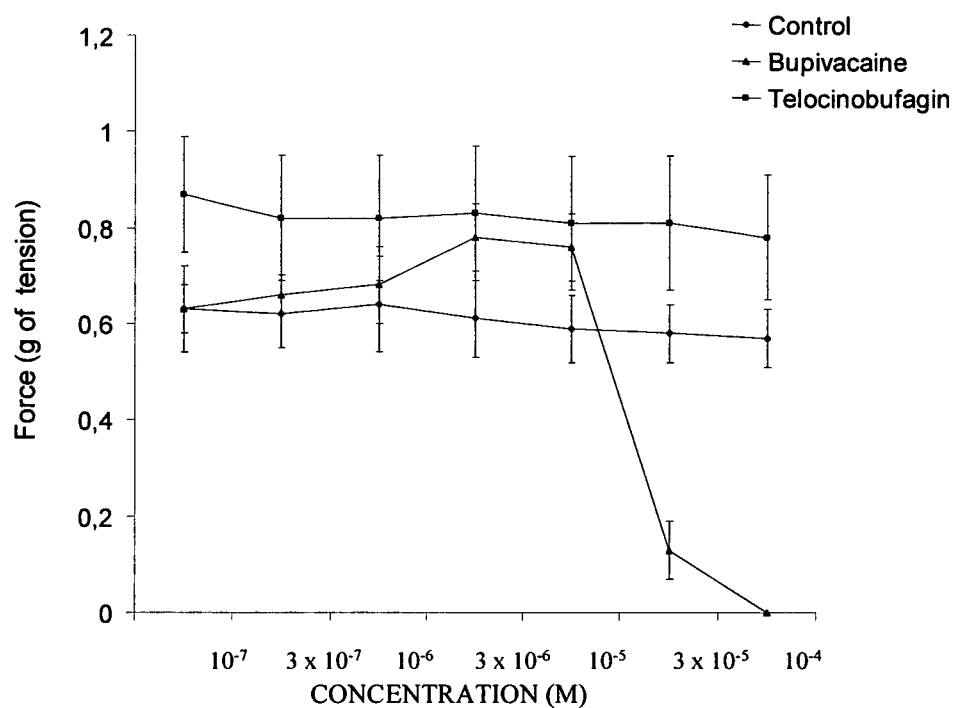
FIG. 26: Effects of ethanol (control), bupivacaine and telocinobufagin at different concentrations ($10^{-7}$ to $10^{-4}$ M) on the cardiac contraction force (inotropism) of rats.

FIG. 26 shows that no significant alteration occurred in the cardiac contraction force in the presence of telocinobufagin at $10^{-7}$ to $10^{-4}$ M concentrations, compared to the control. However, bupivacaine at $3 \times 10^{-5}$ M concentration decreased significantly the cardiac contraction force to 0.13±0.06 g of tension, and the $10^{-4}$ M concentration blocked completely the cardiac contraction force to zero (p<0.05, Dunnett's test). Data are expressed as mean±SEM (n=6). ANOVA and Dunnett's as post-hoc test, p<0.005. a vs control, b vs bupivacaine.

Figure 27:
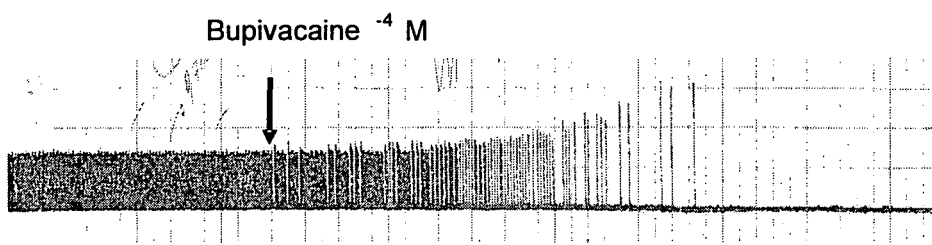
FIG. 27: Polygraphic tracing representing the effect of bupivacaine in the left atrium of rats. The arrows indicate the moment of addition of bupivacaine ($10^{-4}$ M).

FIG. 27 shows a polygraphic tracing representing the effect of bupivacaine in the left atrium of rats. The arrows indicate the moment of the addition of bupivacaine ($10^{-4}$ M).

Figure 28:
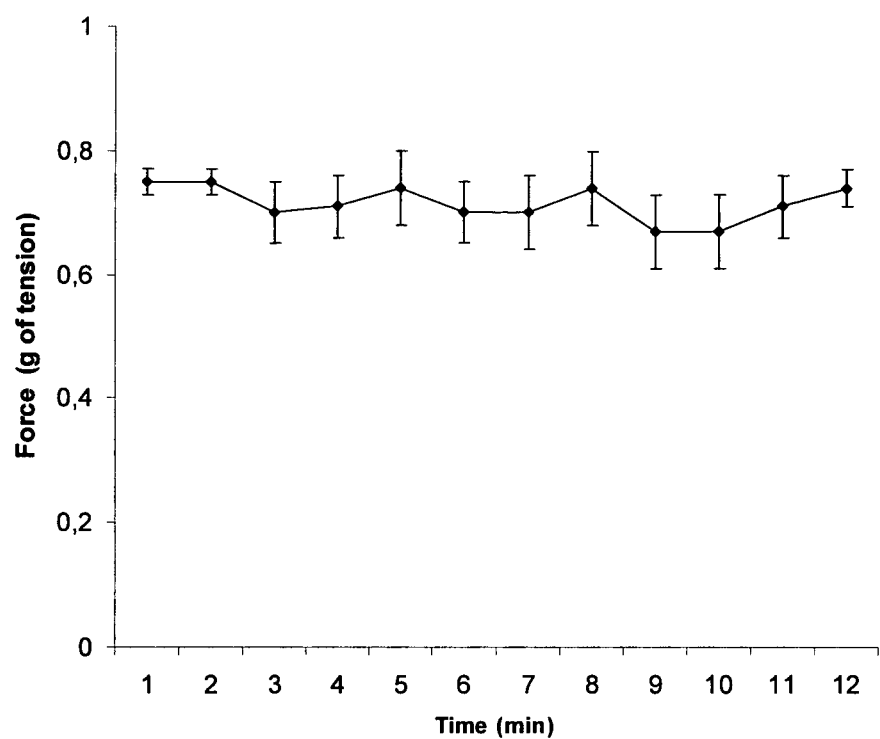
FIG. 28: Effects of telocinobufagin on the cardiac contraction force (inotropism) during 12 minutes of observation using telocinobufagin at $10^{-3}$ M concentration.

In order to determine a toxic dose of telocinobufagin, a concentration of $10^{-3}$ M was used during 12 minutes instead of 5 minutes (FIG. 28). However, even at this concentration, telocinobufagin did not produce significant alteration in the cardiac contraction force (p>0.05, Dunnett's test).

EXAMPLE 7

Effect of Telocinobufagin on the Chronotropism of Isolated Rat Atrium

In order to investigate the possible deleterious effects of telocinobufagin on the heart, the isolated rat atrium model was subsequently used to evaluate the cardiac contraction rate (chronotropism). The right rat atrium was used to assess the chronotropic activity. The values of the spontaneous mechanical activity of the right atrium were expressed in contractions frequency or beats per minute (bpm). The heart rate was 298±50 contractions per minute in the rat right atrium. The response in the frequency of spontaneous cardiac activity did not suffer significant alterations, when the conditions to which the left atrium was subjected in the superperfusion medium were maintained.

Figure 29:
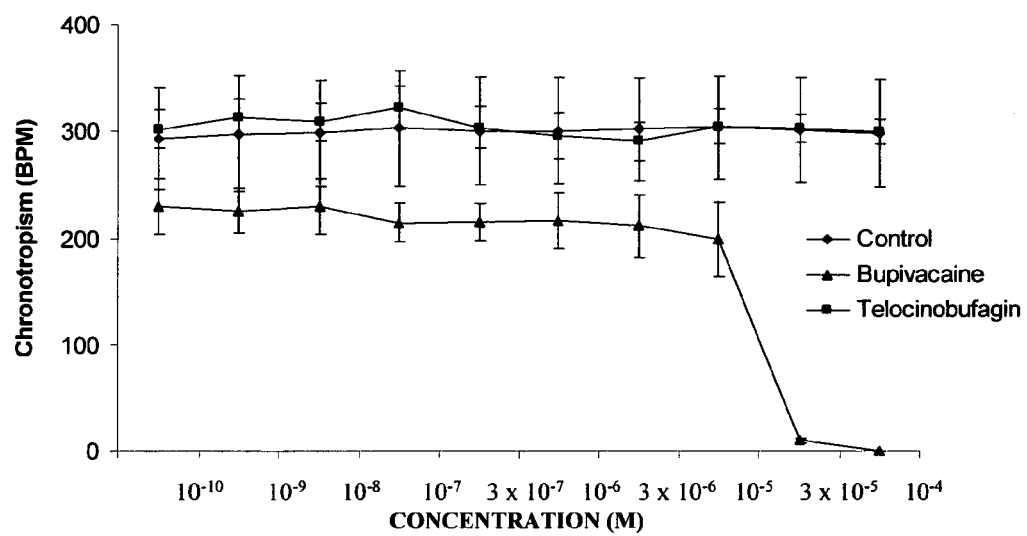
FIG. 29: Effects of ethanol, bupivacaine and telocinobufagin at different concentrations ($10^{-7}$ to $10^{-4}$ M) on the frequency of spontaneous contractions of the right atrium of rats.

FIG. 29 shows that, in the presence of telocinobufagin, no significant alteration was observed on the spontaneous mechanical cardiac activity, compared to the control, at concentrations of $10^{-7}$ M to $10^{-4}$ M (n=6; p>0.05, Dunnett's test). However, bupivacaine decreased significantly the frequency of spontaneous cardiac activity to 9.6±2.4 bpm at the concentration of $3 \times 10^{-5}$ M and blocked completely the heart rate to zero at the concentration of $10^{-4}$ M (p<0.05, Dunnett's test). FIG. 29 demonstrates the effect of bupivacaine and telocinobufagin at different concentrations ($10^{-7}$ M to $10^{-4}$ M) on the frequency of spontaneous contractions of the right atrium of rats. Data are expressed as mean±standard error (n=6). ANOVA and Dunnett's as post-hoc test, p<0.005. a vs control, b vs bupivacaine.

Figure 30:
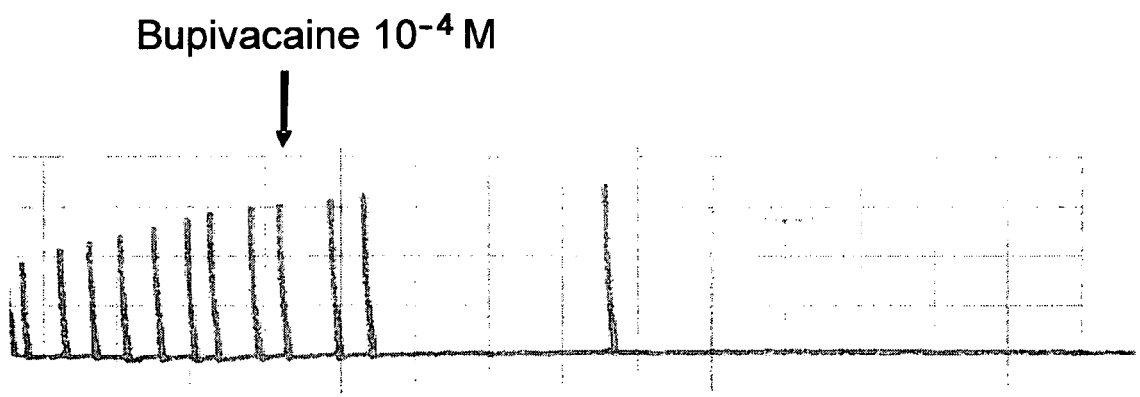
FIG. 30: Polygraphic tracing representing the effect of bupivacaine in the right atrium of rats. The arrows indicate the moment of addition of bupivacaine ($10^{-4}$ M). BS—basal The characteristics of the present invention will become evident from the following detailed description.

FIG. 30 shows a polygraphic tracing representing the effect of bupivacaine on the right rat atrium. The arrows indicate the moment of the addition of bupivacaine ($10^{-4}$ M). BS—basal In Vitro Assays to Evaluate Cardiotoxicity:

EXAMPLE 8

Patch Clamp Assay

The in vitro effects of telocinobufagin in several ion channels were evaluated at room temperature using the PatchXpress® 7000A Automated Parallel Patch-Clamp System (Model 7000A, Molecular Devices, Union City, Calif.). The studies were conducted according to the conventional procedures.

For the assays, a 30 µM telocinobufagin stock solution was prepared in 0.3% DMSO in a buffer solution (HBPS). The assay was evaluated using 15 µM telocinobufagin in 2 cells (n≥2). The exposure duration of each channel was 5 minutes. Telocinobufagin (purity >95%) is insoluble in water, and is soluble in 50% DMSO (v/v in water), ethanol (100%) and pure chloroform. Each record of hKvLQT1/hminK and hCav1.2 (h=human) ended with a supramaximal dose of the positive control (300 µM chromanol and 10 µM nifedipine, respectively). Any left current after exposure to this dose was digitally subtracted to eliminate the contribution of any endogenous current. For this reason, some negative results were obtained for some measures.

The results for telocinobufagin are shown in Table 2. The positive control demonstrated in Table 3 confirms the sensitivity of the test system for ion channel inhibition. Significance criterion: 20% inhibition.

TABLE 2

Results for ion channel inhibition by telocinobufagin.

| Test | | Concentration (µM) | Mean % inhibition | Standard deviation | Standard Error | n |
|---|---|---|---|---|---|---|
| Cav1.2 | | 15 | −0.8 | 1.1 | 0.8 | 2 |
| Cav3.2 | | 15 | 5.7 | 3.0 | 2.1 | 2 |
| HCN2 | | 15 | 3.2 | 0.4 | 0.3 | 2 |
| HCN4 | | 15 | 3.8 | 4.8 | 3.4 | 2 |
| hERG | | 15 | −0.4 | 3.2 | 2.3 | 2 |
| Kir3.1/3.4 | | 15 | −1.8 | 1.6 | 1.1 | 2 |
| Kir6.2/SUR2A | | 15 | 0.3 | 2.1 | 1.5 | 2 |
| Kv1.5 | | 15 | −0.6 | 1.8 | 1.3 | 2 |
| Kv4.3 | | 15 | 3.9 | 2.5 | 1.8 | 2 |
| KvLQT/minK | | 15 | 6.5 | 0.0 | 0.0 | 2 |
| Nav1.5 | Tonic | 15 | 0.8 | 2.9 | 2.0 | 2 |
| | Phasic | 15 | 4.4 | 1.7 | 1.2 | 2 |

TABLE 3

Positive controls for the ion channel inhibition assay.

| Canal | Positive control | Concentration (µM) | Mean % inhibition | Standard deviation | Standard Error | n |
|---|---|---|---|---|---|---|
| Cav1.2 | Nifedipine | 1 | 93.6 | 0.8 | 0.6 | 2 |
| Cav3.2 | Nickel | 100 | 76.6 | 6.1 | 4.3 | 2 |
| HCN2 | Zatebradine | 100 | 96.1 | 5.1 | 3.6 | 2 |
| HCN4 | Zatebradine | 10 | 88.3 | 1.0 | 0.7 | 2 |
| hERG | E-4031 | 0.5 | 101.0 | 1.7 | 1.2 | 2 |
| Kir2.1 | Barium | 100 | 85.4 | 0.1 | 0.1 | 2 |
| Kir3.1/3.4 | Barium | 300 | 86.6 | 0.3 | 0.2 | 2 |

TABLE 3-continued

Positive controls for the ion channel inhibition assay.

| Canal | Positive control | Concentration (µM) | Mean % inhibition | Standard deviation | Standard Error | n |
|---|---|---|---|---|---|---|
| Kir6.2/SUR2A | Glibenclamide | 1 | 79.8 | 2.8 | 2.0 | 2 |
| Kv1.5 | 4-AP | 2000 | 85.1 | 9.9 | 7.0 | 2 |
| Kv4.3 | Flecainide | 100 | 96.1 | 0.3 | 0.2 | 2 |
| KvLQT/minK | Chromanol-293B | 30 | 87.8 | 0.2 | 0.2 | 2 |
| Nav1.5 | Lidocaine | 2000 | 98.5 | 1.9 | 1.3 | 2 |

The results of the inhibition percent mean described in Table 2 show that the several ion channels evaluated were not inhibited by telocinobufagin. Such results corroborate those of the in vivo assays performed to evaluate the effect of telocinobufagin on the inotropism and chronotropism of isolated rat atrium, thus demonstrating absence of cardiotoxicity by telocinobufagin.

In Vitro Assays to Evaluate the Non-Opioid Mechanism of Action:

EXAMPLE 9

Radioligand Binding Assays

The employed methods were adapted from the scientific literature to maximize their reliability and reproducibility. Reference standards were used as an integral part of each assay to assure the validity of the obtained results.

The aim of this assay was to evaluate the activity of telocinobufagin [purity ≧95%] on the opioid receptors. These receptors are currently classified in three groups: µ, δ and κ. The results of this assay are displayed in Table 4 and the employed methods are described below:

Opioid Receptor δ (OP1, DOP)
Source: Human recombinant CHO cells
Ligand: 0.9 nM [$^3$H]Naltrindole
Vehicle: 1% DMSO
Incubation time/temperature: 2 hours at 25° C.
Incubation buffer: Tris-HCl 50 mM, pH 7.4, MgCl$_2$ 5 mM
Non-specific ligand: 10 µM naloxone
$K_D$: 0.49 nM*
$B_{max}$: 8.6 pmole/mg protein
Specific ligation: 80%
Quantitative method: Radioligand binding
Receptor Opioid κ (OP2, KOP)
Source: Human recombinant HEK-293 cells
Ligand: 0.6 nM [$^3$H] Diprenorphine
Vehicle: 1% DMSO
Incubation time/temperature: 60 minutes at 25° C.
Incubation buffer: Tris-HCl 50 mM, pH 7.4
Non-specific ligand: 10 µM naloxone
$K_D$: 0.4 nM
$B_{max}$: 1.1 pmole/mg protein
Specific ligation: 90%
Quantitative method: Radioligand binding
Receptor Opioid µ (OP3, MOP)
Source: Human recombinant CHO-K1 cells
Ligand: 0.6 nM [$^3$H] Diprenorphine
Vehicle: 1% DMSO
Incubation time/temperature: 60 minutes at 25° C.
Incubation buffer: Tris-HCl 50 mM, pH 7.4
Non-specific ligand: 10 µM naloxone
$K_D$: 0.41 nM
$B_{max}$: 3.8 pmole/mg protein
Specific ligation: 90%
Quantitative method: Radioligand binding

TABLE 4

Test of TBC activity in the opioid receptors.
Biochemical tests

| | Telocinobufagin | | | | Reference | |
|---|---|---|---|---|---|---|
| Receptor | Specie | n | Concentration | % Inhibition* | Compound | IC$_{50}$ |
| δ opioid (OP1, DOP) | hum | 2 | 10 µM | 1 | Naltrindole | 1.29 nM |
| k opioid (OP2, KOP) | hum | 2 | 10 µM | 6 | U-69593[a] | 0.0155 µM |
| µ opioid (OP3, MOP) | hum | 2 | 10 µM | −1 | DAMGO[b] | 0.0619 µM | hum = human
*Significance criterion or significant response: ≧50% maximum stimulation or inhibition.
[a]N-Methyl-N-[7-(1-pyrrolidinyl)-1-oxaspiro[4,5]dec-8-yl]benzeneacetamide - k- opioid receptor selective ligand
[b][D-Ala$^2$, NMe-Phe$^4$, Gly-ol$^5$]-enkephalin - highly selective peptide agonist].

The results of the inhibition percent described in Table 4 show that the µ, δ, κ opioid receptors were not inhibited or stimulated by telocinobufagin. These results corroborate with those of the in vivo assays, which showed that the effects of telocinobufagin are not reverted by naloxone. These findings indicate that the mechanism of action of telocinobufagin is not opioid and it is thus expected that this compound is deprived of the adverse side effects of opioids.

The invention claimed is:

1. A method for treating acute or chronic pain, comprising administering, to a human being or animal in need of said treatment, an effective amount of telocinobufagin, or an enantiomer or prodrug thereof that is selected from the group consisting of carbonates, carbamates, phosphates, phosphonates, glycosides, sulfates, fulfonates, ethers and esters of telocinobufagin, optionally in combination with a pharmaceutically acceptable excipient, wherein the pain is acute neurogenic pain or chronic neuropathic pain.

2. The method according to claim 1, wherein the administration to human beings or animals occurs by an oral, sublingual, nasal, rectal, intragingival, endovenous, intramuscular, intraarticular, subcutaneous, inhalatory, transdermal, topical, subarachnoid spinal or peridural spinal route.

3. The method according to claim 1, wherein the administration occurs by the oral route.

4. The method of claim 1, wherein the neuropathic pain is hyperalgesia or allodynia.

* * * * *